US010571253B2

(12) United States Patent
Sato et al.

(10) Patent No.: US 10,571,253 B2
(45) Date of Patent: Feb. 25, 2020

(54) SHAPE ESTIMATION DEVICE, ENDOSCOPE SYSTEM INCLUDING SHAPE ESTIMATION DEVICE, SHAPE ESTIMATION METHOD, AND PROGRAM FOR SHAPE ESTIMATION

(71) Applicant: OLYMPUS CORPORATION, Tokyo (JP)

(72) Inventors: Ken Sato, Hachioji (JP); Hiromasa Fujita, Hachioji (JP); Masanori Mitsui, Machida (JP); Yusuke Yamamoto, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 394 days.

(21) Appl. No.: 15/380,464

(22) Filed: Dec. 15, 2016

(65) Prior Publication Data

US 2017/0095143 A1 Apr. 6, 2017

Related U.S. Application Data

(63) Continuation of application No. PCT/JP2015/064960, filed on May 25, 2015.

(30) Foreign Application Priority Data

Jun. 26, 2014 (JP) .................. 2014-131758

(51) Int. Cl.
*G01B 11/24* (2006.01)
*G01B 11/16* (2006.01)
(Continued)

(52) U.S. Cl.
CPC .......... *G01B 11/24* (2013.01); *A61B 1/00165* (2013.01); *G01B 11/18* (2013.01);
(Continued)

(58) Field of Classification Search
CPC .... A61B 2034/2046; A61B 2034/2061; A61B 5/065; G01B 11/24
See application file for complete search history.

(56) References Cited

U.S. PATENT DOCUMENTS

2007/0116415 A1 5/2007 Kobayashi
2008/0285909 A1* 11/2008 Younge ................ A61B 5/1076
385/13
(Continued)

FOREIGN PATENT DOCUMENTS

CN 105473980 A 4/2016
JP 2003-515104 A 4/2003
(Continued)

OTHER PUBLICATIONS

Chinese Office Action dated Aug. 23, 2017 in Chinese Patent Application No. 201580034488.2.
(Continued)

*Primary Examiner* — Aaron B Fairchild
(74) *Attorney, Agent, or Firm* — Scully, Scott, Murphy & Presser, P.C.

(57) ABSTRACT

A shape estimation device includes an input circuit, a storage circuit and an arithmetic circuit. The input circuit receives light amount information being a relationship between a wavelength and a light amount. The light amount information is acquired by using a sensor configured such that the light amount to be detected with respect to the wavelength corresponding to each of sensing parts varies in accordance with a shape of each of the sensing parts. The storage circuit stores a relationship among the shape, the wavelength and the light amount with respect to each sensing part. The arithmetic circuit calculates the shape of each sensing part,
(Continued)

based on the light amount information, and a light amount estimation value being a relationship between the wavelength and the light amount.

16 Claims, 18 Drawing Sheets

(51) Int. Cl.
　　*G02B 23/24* 　　(2006.01)
　　*A61B 1/00* 　　(2006.01)
　　*A61B 34/20* 　　(2016.01)
　　*G02B 6/14* 　　(2006.01)
(52) U.S. Cl.
　　CPC ...... *G02B 23/24* (2013.01); *A61B 2034/2061* (2016.02); *G02B 6/14* (2013.01); *G02B 23/2469* (2013.01)

(56) References Cited

U.S. PATENT DOCUMENTS

| | | | |
|---|---|---|---|
| 2011/0218404 A1 | 9/2011 | Hirakawa | |
| 2013/0308138 A1* | 11/2013 | 'T Hooft | G01B 11/18 356/601 |
| 2014/0036261 A1 | 2/2014 | Fujita et al. | |
| 2016/0166130 A1 | 6/2016 | Fujita et al. | |

FOREIGN PATENT DOCUMENTS

| | | |
|---|---|---|
| JP | 2007-143600 A | 6/2007 |
| JP | 2011-30735 A | 2/2011 |
| JP | 2014-76174 A | 5/2014 |
| WO | 01/332165 A1 | 5/2001 |
| WO | 2010/140440 A1 | 12/2010 |

OTHER PUBLICATIONS

Japanese Office Action dated Oct. 31, 2017 in Japanese Patent Application No. 2014-131758.
English translation of International Preliminary Report on Patentability dated Jan. 5, 2017 together with the Written Opinion received in related International Application No. PCT/JP2015/064960.
German Office Action dated Nov. 15, 2017 in German Patent Application No. 11 2015 003 001.8.
German Search Report dated Nov. 14, 2017 in German Patent Application No. 11 2015 003 001.8.
International Search Report dated Jun. 23, 2015 received in International Application No. PCT/JP2015/064960, together with an English-language translation.

* cited by examiner

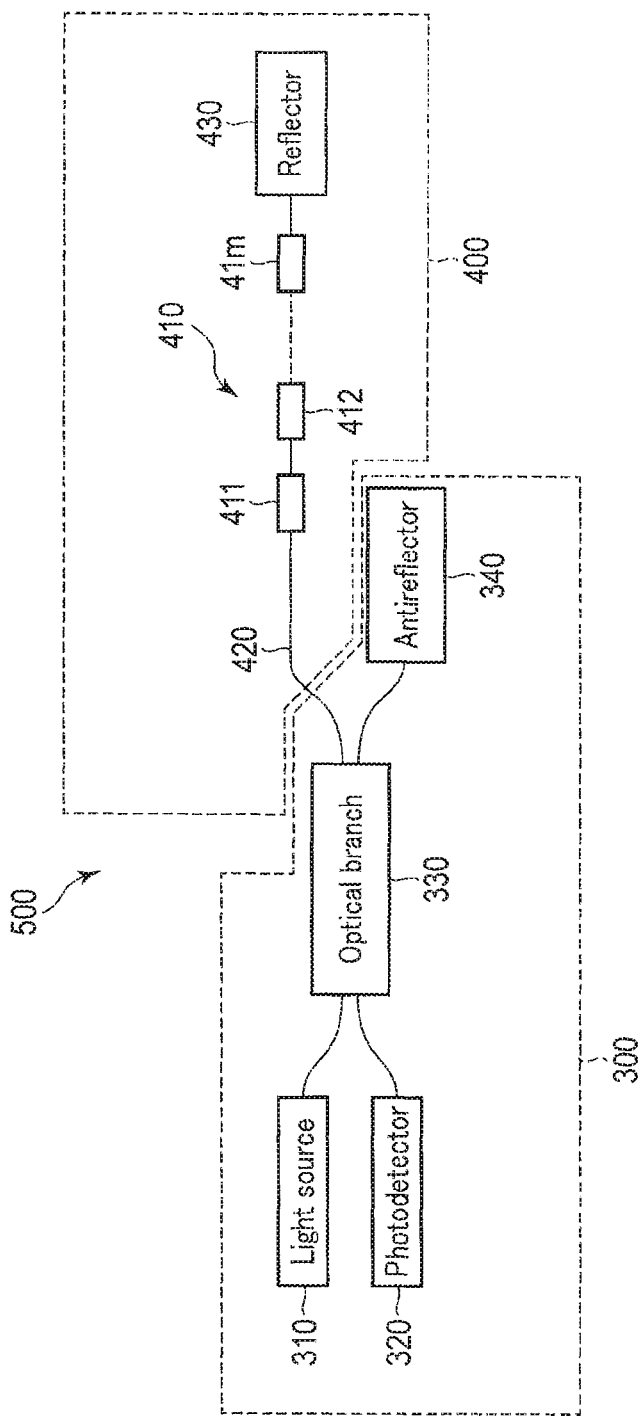
F I G. 2

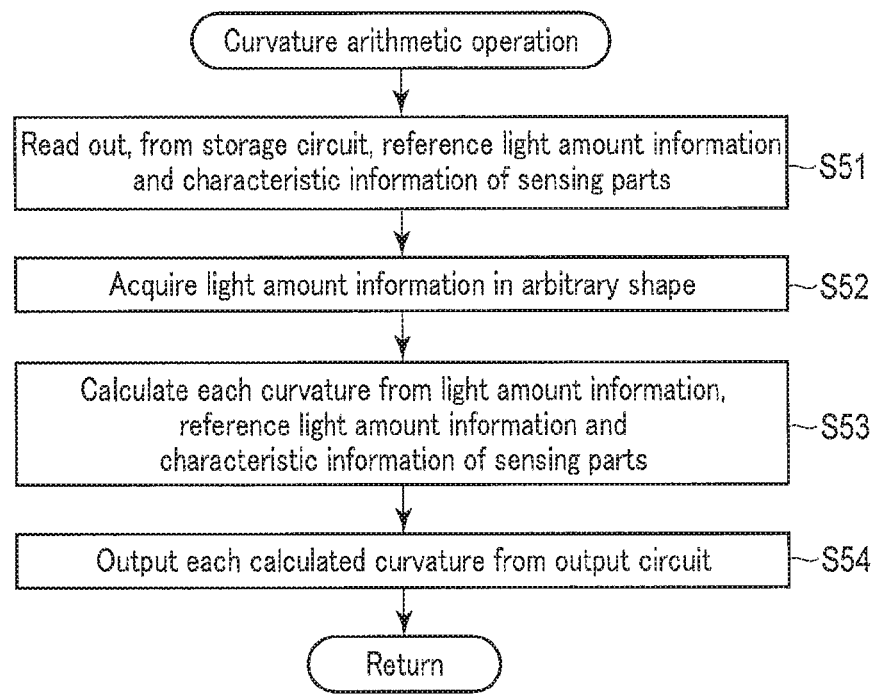
F I G. 20

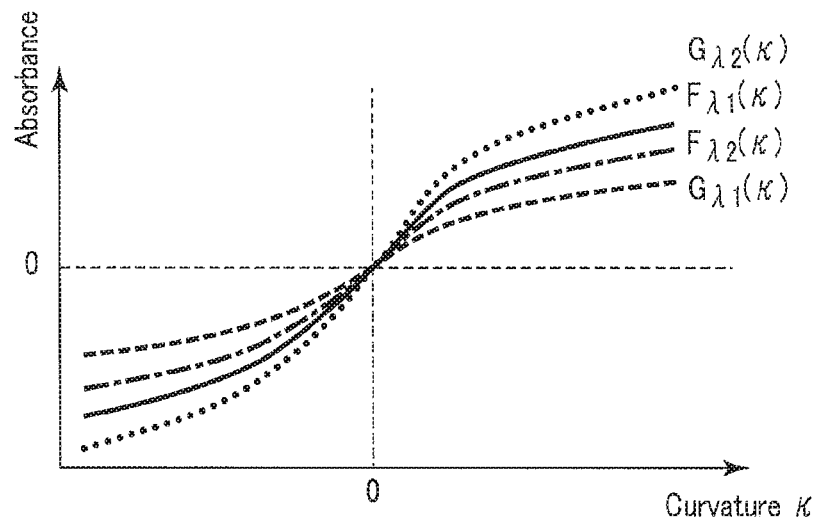
F I G. 22
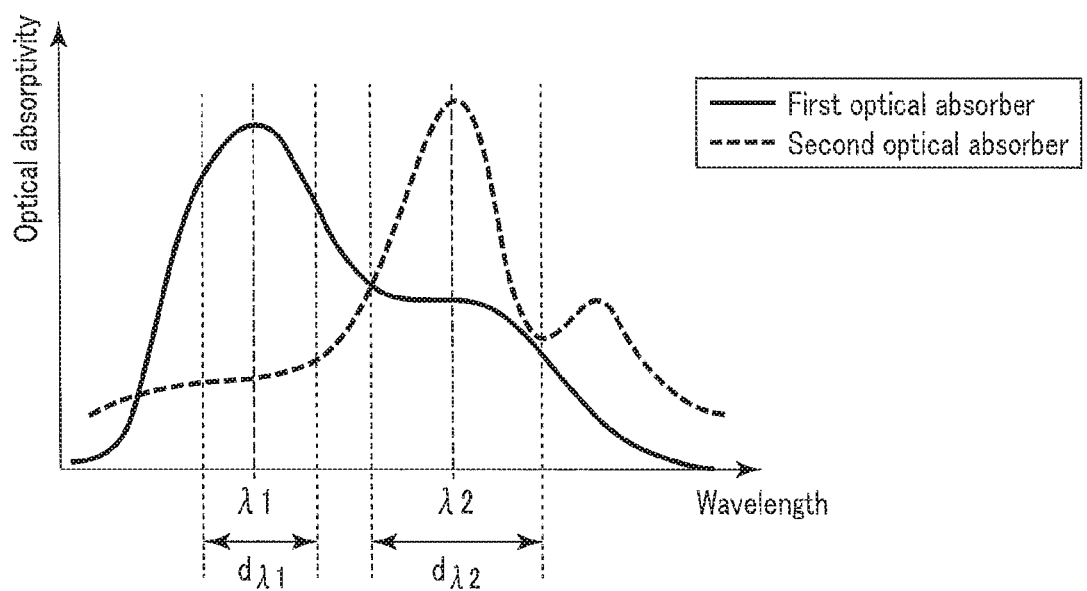
F I G. 23

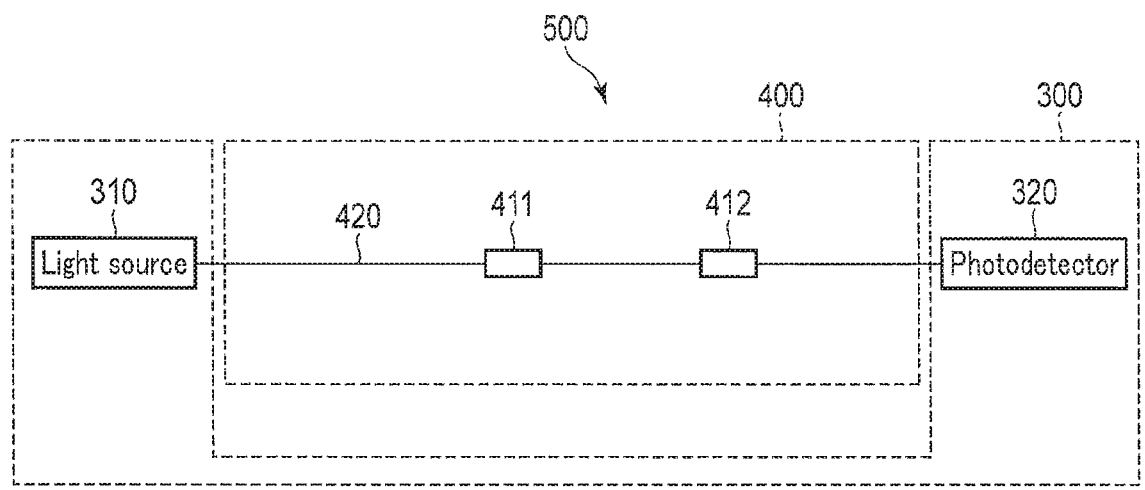
F I G. 24
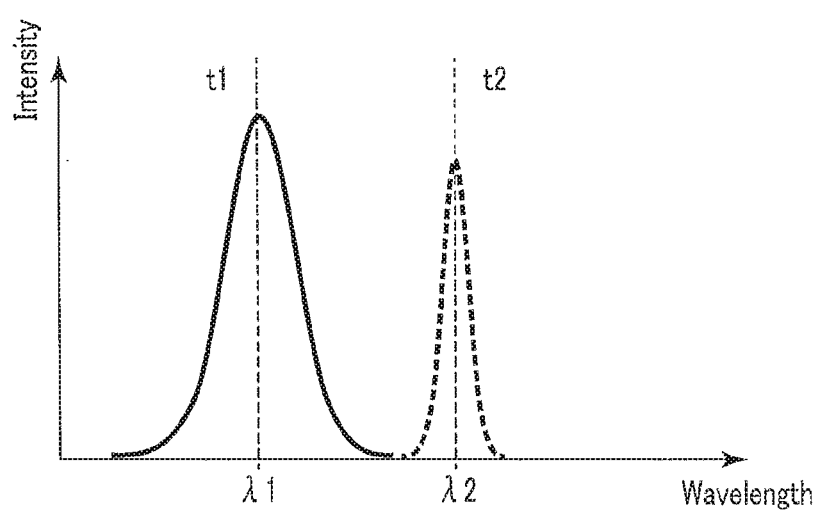
F I G. 25

SHAPE ESTIMATION DEVICE, ENDOSCOPE SYSTEM INCLUDING SHAPE ESTIMATION DEVICE, SHAPE ESTIMATION METHOD, AND PROGRAM FOR SHAPE ESTIMATION

CROSS-REFERENCE TO RELATED APPLICATIONS

This application is a Continuation application of PCT Application No. PCT/JP2015/064960, filed May 25, 2015 and based upon and claiming the benefit of priority from prior the Japanese Patent Application No. 2014-131758, filed Jun. 26, 2014, the entire contents of all of which are incorporated herein by references.

BACKGROUND OF THE INVENTION

1. Field of the Invention

The present invention relates to a shape estimation device which estimates a bend shape of an object with flexibility, an endoscope system including the shape estimation device, a shape estimation method, and a program for shape estimation.

2. Description of the Related Art

There is known a device which is assembled in an insertion apparatus including an insertion section with flexibility, for example, in an insertion section of an endoscope, thereby detecting the shape of the insertion section. For example, Jpn. Pat. Appln. KOKAI Publication No. 2007-143600 discloses a shape detection probe which employs an optical fiber provided with an optical modulation section as a sensing part. The shape detection probe includes an optical fiber which bends as one piece with an insertion section of an endoscope. The optical fiber transmits lights with wavelength components being different from each other, and the optical modulation section modulates the intensity, etc. of the wavelength components of the transmitted lights. In the shape detection probe, the shape of the optical fiber at the optical modulation section, and, therefore, the shape of the endoscope, which bends as one piece with the optical fiber, is detected based on the intensity, etc. of wavelength components before and after modulation by the optical modulation section.

BRIEF SUMMARY OF THE INVENTION

One embodiment of the present invention is a shape estimation device comprising an input circuit, a storage circuit, and a shape arithmetic circuit. The input circuit is configured to receive light amount information which is a relationship between a wavelength and a light amount, the light amount information being acquired by using a sensor configured such that the light amount to be detected with respect to the wavelength corresponding to each of a plurality of sensing parts varies in accordance with a shape of each of the plurality of sensing parts. The storage circuit is configured to store a light amount estimation relationship including shape characteristic information representing a relationship among the shape, the wavelength and the light amount with respect to each of the plurality of sensing parts. The shape arithmetic circuit is configured to calculate the shape of each of the plurality of sensing parts, based on the light amount information, and a light amount estimation value which is a relationship between the wavelength and the light amount, the light amount estimation value being calculated based on the light amount estimation relationship.

Other embodiment of the present invention is an endoscope system comprising the above-described shape estimation device, an endoscope configured such that a light guide is provided in an insertion section; and an endoscope shape calculator configured to calculate a shape of the insertion section, based on the shape characteristic information.

Other embodiment of the present invention is a shape estimation method comprising acquiring light amount information which is a relationship between a wavelength and a light amount, the light amount information being acquired by using a sensor configured such that the light amount to be detected with respect to the wavelength corresponding to each of a plurality of sensing parts varies in accordance with a shape of each of the plurality of sensing parts, acquiring a light amount estimation relationship including shape characteristic information representing a relationship among the shape, the wavelength and the light amount with respect to each of the plurality of sensing parts; and calculating the shape of each of the plurality of sensing parts, based on the light amount information, and a light amount estimation value which is a relationship between the wavelength and the light amount, the light amount estimation value being calculated based on the light amount estimation relationship.

Furthermore, other embodiment of the present invention is a program for shape estimation, which causes a computer to execute acquiring light amount information which is a relationship between a wavelength and a light amount, the light amount information being acquired by using a sensor configured such that the light amount to be detected with respect to the wavelength corresponding to each of a plurality of sensing parts varies in accordance with a shape of each of the plurality of sensing parts, acquiring a light amount estimation relationship including shape characteristic information representing a relationship among the shape, the wavelength and the light amount with respect to each of the plurality of sensing parts, and calculating the shape of each of the plurality of sensing parts, based on the light amount information, and a light amount estimation value which is a relationship between the wavelength and the light amount, the light amount estimation value being calculated based on the light amount estimation relationship.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing an example of the configuration of a sensor.

FIG. 20 is a flowchart showing an example of a curvature arithmetic process.

FIG. 22 is a graph showing an example of the relationship between curvature and light absorbance of the first sensing part and the second sensing part.

FIG. 23 is a graph showing an example of the relationship between light wavelengths and absorptivities in the first optical absorber and the second optical absorber.

FIG. 24 is a block diagram showing an example of the configuration of the sensor.

FIG. 25 is a graph showing an example of the relationship between wavelength and light emission intensity of the light source at a certain time instant.

DETAILED DESCRIPTION OF THE INVENTION

First Embodiment

Figure 1:
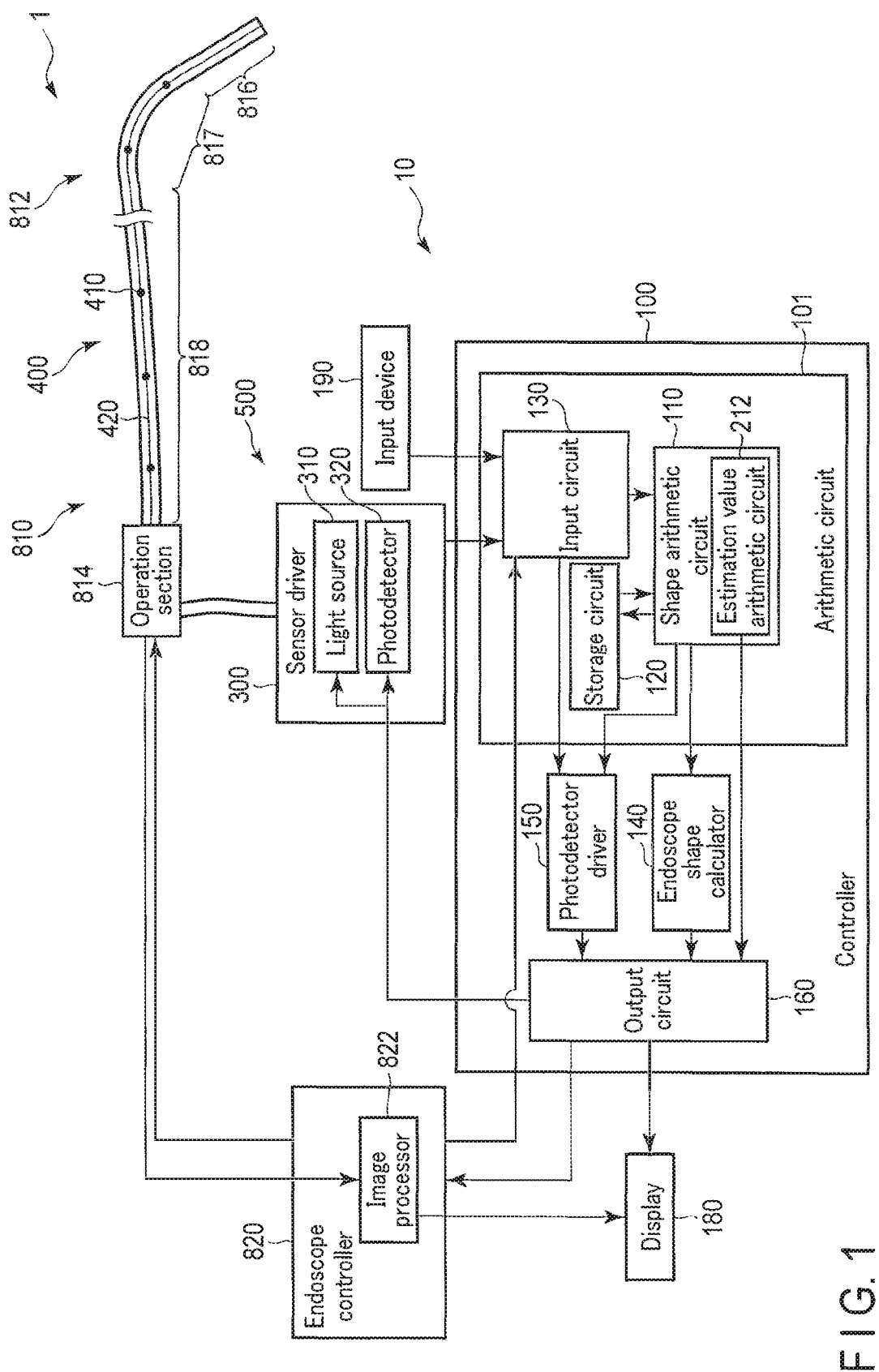
FIG. 1 is a view which schematically shows the configuration of an endoscope system including a shape estimation device according to a first embodiment.

FIG. 1 is a view which schematically shows the configuration of an endoscope system 1 including a shape estimation device 10 according to a first embodiment of the present invention. The endoscope system 1 includes an endoscope 810, an endoscope controller 820, the shape estimation device 10, a display 180, and an input device 190.

The endoscope 810 includes an insertion section 812 which is to be inserted into an insertion target, and an operation section 814 which is coupled to a proximal end side of the insertion section 812. The insertion section 812 is an elongated tubular portion on an endoscope distal-end side, and includes a distal rigid portion 816, a bending portion 817 provided on a proximal-end side of the distal rigid portion 816, and a flexible tube portion 818 provided on a proximal-end side of the bending portion 817. In the distal rigid portion 816, an illumination optical system, an observation optical system, an image sensor, etc., which are not shown, are incorporated. The bending portion 817 is bent in a desired direction by operating the operation section 814. The flexible tube portion 818 is free to bend, and, for example, the flexible tube portion 818 bends along the bend shape of the insertion target. The operation section 814 performs various kinds of operations of the endoscope 810, including the above-described bending operation among others.

The endoscope controller 820 controls various operations of the endoscope 810. In addition, the endoscope controller 820 includes an image processor 822 for processing an image acquired by the observation optical system and the image sensor of the endoscope 810.

The shape estimation device 10 is a device for estimating a bend shape of the insertion section 812 of the endoscope 810, in particular, the bending portion 817 or flexible tube portion 818. The shape estimation device 10 includes a sensor 500 including a sensor driver 300 and a sensor unit 400; and a controller 100. The details of these will be described later.

The display 180 is a general display device, and is, for instance, a liquid crystal display, a CRT display, or an organic EL display. The display 180 is connected to the endoscope controller 820, and displays an image acquired by the endoscope 810. In addition, the display 180 is connected to the controller 100 of the shape estimation device 10, and displays information of the shape of the insertion section 812 of the endoscope 810, the information being acquired by the shape estimation device 10.

The input device 190 is a general device for input, and is, for instance, a keyboard, a mouse, a pointing device, a tag reader, a button switch, a slider, or a dial. The input device 190 is connected to the controller 100 of the shape estimation device 10. The input device 190 is used in order for a user to input various instructions for operating the shape estimation device 10. The input device 190 may be a storage medium. In this case, the information stored in the storage medium is input to the controller 100.

Next, the sensor 500 of the shape estimation device 10 will be described. FIG. 2 is a block diagram showing an example of the configuration of the sensor 500 including the sensor driver 300 and the sensor unit 400. The sensor driver 300 includes a light source 310, a photodetector 320, an optical branch 330, and an antireflector 340. The sensor unit 400 includes a light guide 420 provided with a plurality of sensing parts 410; and a reflector 430.

The light source 310 is, for example, a generally known light emission unit, such as a lamp, an LED, or a laser diode. The light source 310 may further include a fluorescent element for converting wavelength.

Figure 3:
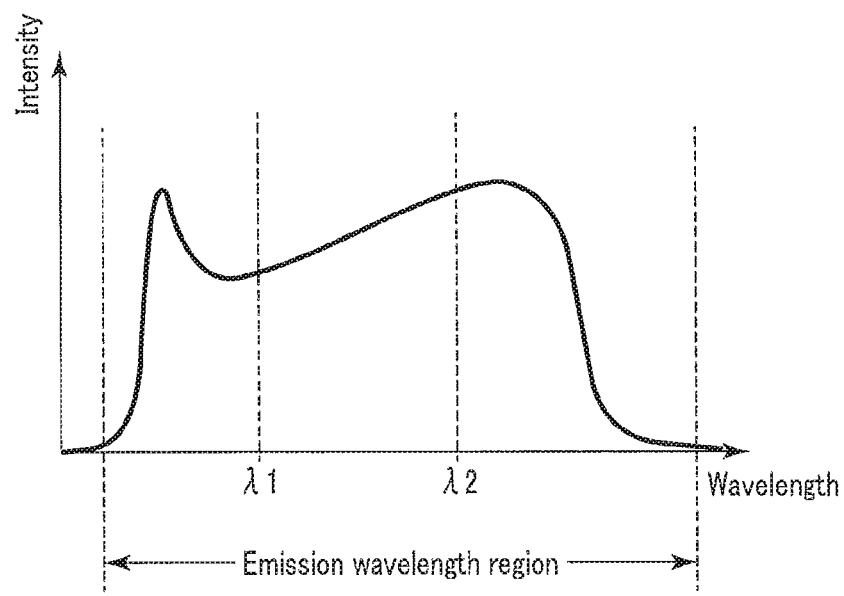
FIG. 3 is a graph showing an example of the relationship between the wavelength and intensity of light which is emitted by a light source.

FIG. 3 is a graph showing an example of the relationship between the wavelength and intensity of light which is emitted by the light source 310. The light source 310 emits light in an emission wavelength region including a first wavelength $\lambda 1$ and a second wavelength $\lambda 2$. The first wavelength $\lambda 1$ is a characteristic wavelength of a spectrum which an optical absorber of a first sensing part 411 (to be described later) of the sensor unit 400 absorbs. Here, the characteristic wavelength is, for example, a wavelength at which absorption becomes maximum (see FIG. 7). Similarly, the second wavelength $\lambda 2$ is a characteristic wavelength of a spectrum which an optical absorber of a second sensing part 412 (to be described later) of the sensor unit 400 absorbs.

The photodetector 320 includes an element for separation of light into its spectral components, such as a spectroscope or a color filter; and a light receiving element such as a photodiode. The photodetector 320 detects the intensity of light in a predetermined wavelength region, and outputs light amount information. Here, the light amount information is information indicative of the relationship between a specific wavelength in the predetermined wavelength region and the intensity of light at the wavelength.

Figure 4:
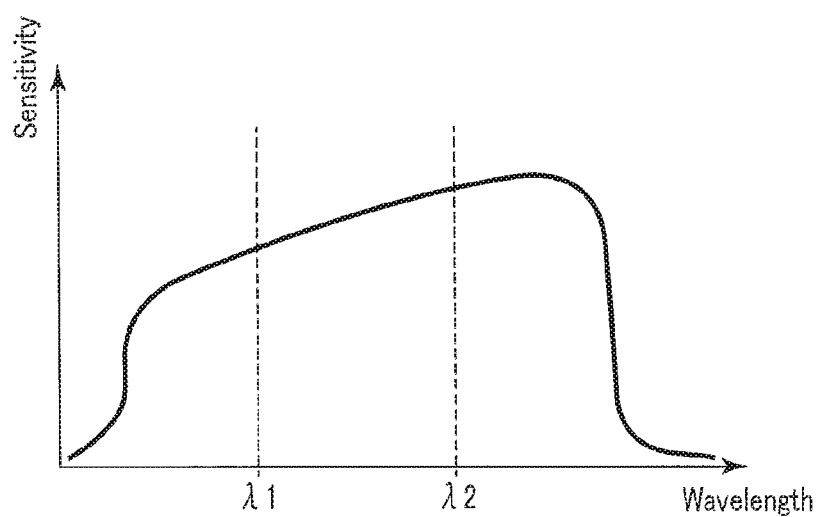
FIG. 4 is a graph showing an example of the relationship between the wavelength of light, which falls on a photodetector, and the detection sensitivity of the photodetector.

FIG. 4 is a graph showing an example of the relationship between the wavelength of light, which falls on the photodetector 320, and the detection sensitivity of the photodetector 320. The photodetector 320 has detection sensitivity within a wavelength region including the above-described first wavelength $\lambda 1$ and second wavelength $\lambda 2$. The photodetector 320 outputs the detected light intensities, for example, at the first wavelength $\lambda 1$ and second wavelength $\lambda 2$, to the controller 100.

The photodetector is not limited to a photodetector having spectral characteristics. The light source and photodetector include an mode in which light amounts at a plurality of predetermined wavelength regions are detected by a combination of a light source and a photodetector. For example, the light source and photodetector include an mode in which narrow-band lights are emitted from a light source in a time-sequence manner, and light amounts at the respective wavelength regions are detected by a wide-band photodetector.

The optical branch 330 is optically connected to the light source 310 and the photodetector 320. The optical branch 330 includes an optical coupler or a semitransparent mirror. The optical branch 330 guides light emitted from the light source 310 to the light guide 420 (to be described later) of the sensor unit 400, and guides light guided by the light guide 420 to the photodetector 320.

The antireflector 340 is optically connected to the optical branch 330. The antireflector 340 prevents a part of the light emitted from the light source 310, which did not enter the light guide 420, from returning to the photodetector 320.

The light guide 420 is, for example, an optical fiber, and has flexibility. The light guide 420 is connected to the optical branch 330 at its proximal end. As schematically shown in FIG. 1, the light guide 420 is incorporated into the insertion section 812 of the endoscope 810 along the longitudinal direction of the insertion section 812. The sensing parts 410 of the light guide 420 are arranged on a region where the shape is to be calculated in the insertion section 812, for example, on the bending portion 817 or flexible tube portion 818.

The light guide 420 is provided with the plurality of sensing parts 410. The sensing parts 410 include a first sensing part 411 and a second sensing part 412, and may further include an m-th sensing part 41$m$. Here, "m" is an arbitrary number. These sensing parts 410 are arranged at different positions in the longitudinal direction (optical-axis direction) of the light guide 420, that is, are spaced from each other. Hereinafter, it is assumed that the light guide 420 is provided with two sensing parts 410, namely the first sensing part 411 and second sensing part 412, and the description will be given.

Figure 5:
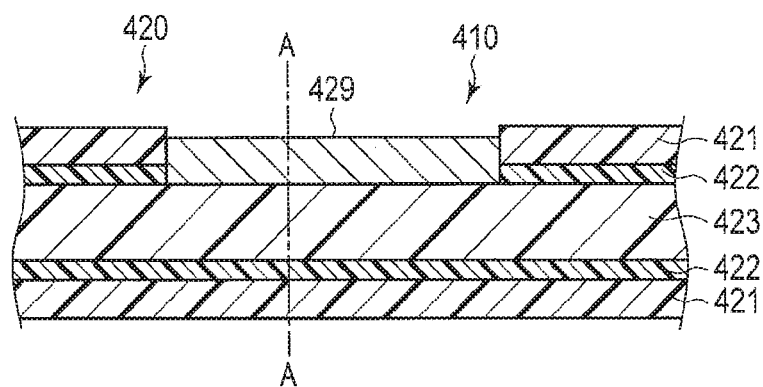
FIG. 5 is a cross-sectional view including an optical axis of a light guide.
Figure 6:
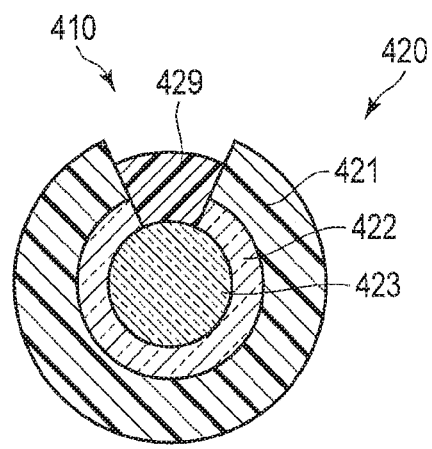
FIG. 6 is a cross-sectional view in a radial direction of the light guide, FIG. 6 being taken along line A-A in FIG. 5.

FIG. 5 is a cross-sectional view including an optical axis of the light guide 420. FIG. 6 is a cross-sectional view in a radial direction of the light guide 420, FIG. 6 being taken along line A-A in FIG. 5. The light guide 420 includes a core 423, a cladding 422 surrounding the core 423, and a jacket 421 surrounding the cladding 422.

The sensing part 410 is formed such that the core 423 is exposed by removing parts of the jacket 421 and cladding 422, and an optical absorber 429 is provided on the exposed core 423. Optical absorbers 429 having different light absorptivities at respective wavelengths, that is, having different optical modulation characteristics, are used for the sensing parts 410, respectively. Hereinafter, the optical absorber 429 provided in the first sensing part 411 is referred to as "first optical absorber", and the optical absorber 429 provided in the second sensing part 412 is referred to as "second optical absorber". Aside from the optical absorber, an optical member which affects the spectrum of light guided may be used. For example, the optical member may be a wavelength conversion member (fluorescent element)

Figure 7:
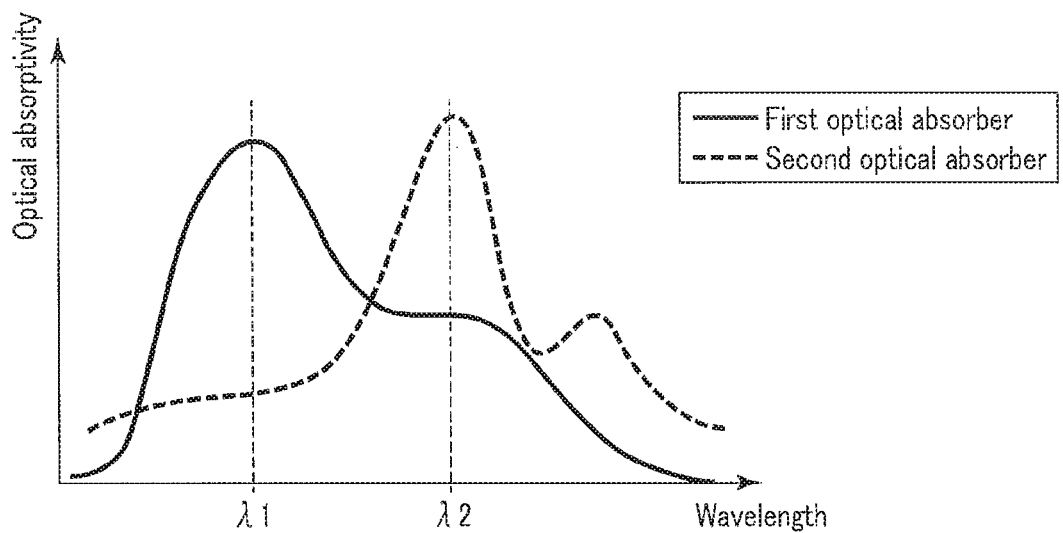
FIG. 7 is a graph showing an example of the relationship between the wavelengths of light and absorptivities in a first optical absorber and a second optical absorber.

FIG. 7 is a graph showing an example of the relationship between the wavelengths of light and absorptivities in the first optical absorber and second optical absorber. In FIG. 7, a solid line indicates absorption characteristics of the first optical absorber, and a broken line indicates absorption characteristics of the second optical absorber. As shown in FIG. 7, the optical absorbers provided in the different sensing parts 410 have absorption characteristics being different from each other.

There may be a case in which a degree of absorption occurs over the entirety of the emission wavelength region, as indicated by the absorptivity of the second optical absorber shown in FIG. 7, depending on the area of contact between the core 423 and optical absorber 429, the refractive index of the optical absorber, and the absorption characteristics. Even in such a case, the curvature of each sensing part 410 can be calculated by taking into account a variation ratio in each sensing part 410, which will be described later.

Figure 8A:
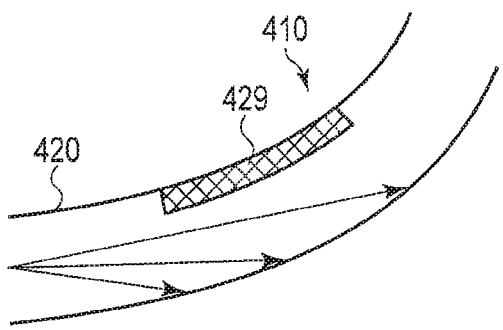
FIG. 8A is a view which schematically shows transmission of light in a state in which a sensing part bends inward.
Figure 8B:
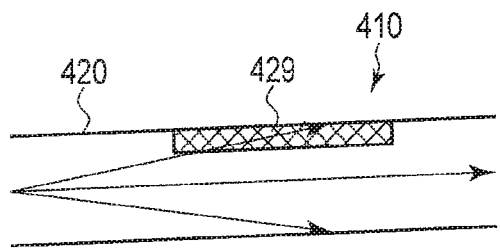
FIG. 8B is a view which schematically shows transmission of light in a state in which the sensing part is straight.
Figure 8C:
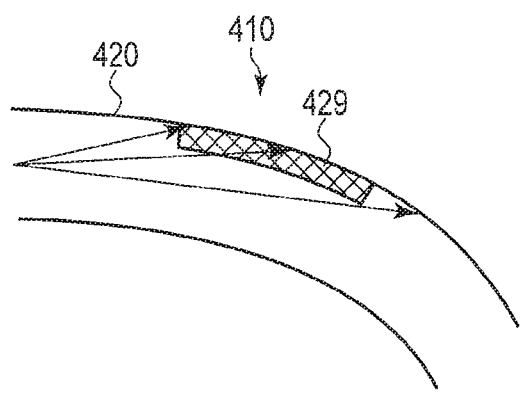
FIG. 8C is a view which schematically shows transmission of light in a state in which the sensing part bends outward.

A description will be given of the relationship between the bend of the sensing part 410 and the transmission amount of light which is guided in the light guide 420. FIG. 8A to 8C are views which schematically show light that is guided in the vicinity of the sensing part 410 of the light guide 420. As shown in FIG. 8B, when the light guide 420 is in a straight state, part of the light, which is guided in the light guide 420, is absorbed in the optical absorber 429. By contrast, when the light guide 420 bends such that the optical absorber 429 is located inside, the light fell on the optical absorber 429 decreases, and thus the amount of light absorbed by the optical absorber 429 decreases (FIG. 8A). Accordingly, the transmission amount of light guided in the light guide 420 increases. On the other hand, when the light guide 420 bends such that the optical absorber 429 is located outside, the light fell on the optical absorber 429 increases, and thus the amount of light absorbed by the optical absorber 429 increases (FIG. 8C). Accordingly, the transmission amount of light guided in the light guide 420 decreases.

Thus, in accordance with the bend of the sensing part 410, the amount of light guided in the light guide 420 varies. In the description below, it is assumed that the bend of the light guide 420 in such a direction that the transmission amount of light by the light guide 420 increases, as shown in FIG. 8A, is the bend in a positive direction, and that the bend of the light guide 420 in such a direction that the transmission amount of light by the light guide 420 decreases, as shown in FIG. 8C, is the bend in a negative direction.

Referring back to FIG. 2, the reflector 430 is provided at an end portion of the light guide 420, that is, a distal end thereof, on the side on which the light guide 420 is not connected to the optical branch 330. The reflector 430 reflects the light guided from the optical branch 330 by the light guide 420, such that the light travels back toward the optical branch 330.

Next, referring back to FIG. 1, the controller 100 of the shape estimation device 10 will be described. The controller 100 is composed of an electronic calculator which is, for instance, a personal computer. The controller 100 includes an arithmetic circuit 101, an endoscope shape calculator 140, a photodetector driver 150, and an output circuit 160.

The arithmetic circuit 101 is composed of, for example, a device including a CPU or an ASIC. The arithmetic circuit 101 includes an input circuit 130, a storage circuit 120, and a shape arithmetic circuit 110.

Light amount information is input to the input circuit 130 from the photodetector 320 of the sensor driver 300. The input circuit 130 transmits the input light amount information to the shape arithmetic circuit 110. In addition, shape characteristic information (to be described later) of the sensing parts 410 is input to the input circuit 130. Further, information output from the endoscope controller 820 is input to the input circuit 130. The input circuit 130 transmits these input signals to the photodetector driver 150 or shape arithmetic circuit 110.

The storage circuit 120 stores various kinds of information being necessary for arithmetic operations that are executed by the shape arithmetic circuit 110. The storage circuit 120 stores, for example, programs including a calculation algorithm, and a light amount estimation relationship including shape characteristic information (to be described later) of the sensing parts 410.

The shape arithmetic circuit 110 calculates the shape of each sensing part 410, based on the light amount information acquired via the input circuit 130 and the light amount estimation relationship (to be described later) stored in the storage circuit 120. The shape arithmetic circuit 110 includes an estimation value arithmetic circuit 212. The estimation value arithmetic circuit 212 generates a light amount estimation value, based on the light amount estimation relationship stored in the storage circuit 120. The shape arithmetic circuit 110 calculates the shape of each sensing part 410, based on the light amount information acquired via the input circuit 130 and the light amount estimation value. The shape arithmetic circuit 110 transmits the calculated shape of the sensing part 410 to the endoscope shape calculator 140 and output circuit 160. In addition, the shape arithmetic circuit 110 outputs to the photodetector driver 150 the information relating to the operation of the photodetector 320 being necessary for the shape calculation, such as a gain of the photodetector 320.

The endoscope shape calculator 140 includes, for example, a CPU or an ASIC. Based on the shape of each sensing part 410 calculated by the shape arithmetic circuit 110, the endoscope shape calculator 140 calculates the shape of the insertion section 812 of the endoscope 810 in which the sensing parts 410 are arranged. The calculated shape of the insertion section 812 is transmitted to the output circuit 160. The endoscope shape calculator 140 may be assembled in the shape arithmetic circuit 110.

The photodetector driver 150 generates a driving signal of the photodetector 320, based on the information acquired from the input circuit 130 or shape arithmetic circuit 110. By the driving signal, the photodetector driver 150 switches on/off the operation of the photodetector 320, for example, based on the user's instruction which is input to the input device 190 and is acquired via the input circuit 130, or adjusts the gain of the photodetector 320, based on the information acquired from the shape arithmetic circuit 110. The photodetector driver 150 may be configured to also control the operation of the light source 310. The photodetector driver 150 transmits the generated driving signal to the output circuit 160.

The output circuit 160 outputs to the display 180 the shape of the sensing part 410 acquired from the shape arithmetic circuit 110 or the shape of the insertion section 812 acquired from the endoscope shape calculator 140. The output circuit 160 also outputs to the endoscope controller 820 the shape of the sensing part 410 acquired from the shape arithmetic circuit 110 or the shape of the insertion section 812 acquired from the endoscope shape calculator 140. The output circuit 160 also outputs the driving signal from the photodetector driver 150 to the photodetector 320.

The operation of the endoscope system 1 and shape estimation device 10 of the present embodiment will be described.

The insertion section 812 of the endoscope 810 is inserted into an insertion target by the user. During insertion, the insertion section bends in accordance with the shape of the insertion target. The endoscope 810 acquires an image signal by the observation optical system and the image sensor provided in the distal rigid portion 816 of the insertion section 812. The acquired image signal is transmitted to the image processor 822 of the endoscope controller 820. The image processor 822 creates an endoscopic image, based on the acquired image signal. The image processor 822 causes the display 180 to display the created endoscopic image.

When the user wishes to cause the display 180 to display the shape of the insertion section 812, or when the user wishes to cause the endoscope controller 820 to perform various operations using the shape of the insertion section 812, the user inputs the corresponding instruction to the controller 100 through the input device 190. Then, the shape estimation device 10 operates.

If the shape estimation device 10 operates, the light source 310 of the sensor driver 300 emits light of a predetermined emission wavelength region. The light emitted from the light source 310 is guided to the light guide 420 of the sensor unit 400 via the optical branch 330. The guided light transmits in the light guide 420 from the proximal-end side to the distal-end side. At this time, the light amount in the light guide 420 varies in accordance with the bend states of the sensing parts 410 provided on the light guide 420, and the amount of transmitted light decreases at each wavelength. Then, the light is reflected and returned by the reflector 430, and transmits in the light guide 420 from the distal-end side to the proximal-end side. The reflected light reaches the photodetector 320 via the optical branch 330. The photodetector 320 detects the intensity of the reached light at each wavelength.

The photodetector 320 outputs light amount information, which relates to the wavelength and the detected light intensity, to the input circuit 130 of the controller 100. The input light amount information is acquired by the shape arithmetic circuit 110 from the input circuit 130, and the shape arithmetic circuit 110 calculates the shape of each sensing part 410.

The information of the shape of each sensing part 410 calculated by the shape arithmetic circuit 110 is acquired by the endoscope shape calculator 140. Based on the shapes of the sensing parts 410, the endoscope shape calculator 140 calculates the shape of the insertion section 812 of the endoscope 810.

The information of the shape of each sensing part 410 calculated by the shape arithmetic circuit 110, or the shape of the insertion section 812 calculated by the endoscope shape calculator 140, is acquired by the endoscope controller 820 via the output circuit 160. Based on the information of the shape of each sensing part 410 or the shape of the insertion section 812, the endoscope controller 820 controls the operation of the endoscope 810.

In addition, the shape of each sensing part 410 calculated by the shape arithmetic circuit 110, or the shape of the insertion section 812 calculated by the endoscope shape calculator 140, is displayed on the display 180 via the output circuit 160.

Furthermore, the information input to the input circuit 130 and the information of the shape of each sensing part 410 calculated by the shape arithmetic circuit 110 are acquired by the photodetector driver 150. Based on the acquired information, the photodetector driver 150 transmits a driving signal to the photodetector 320 via the output circuit 160, and controls the operation of the photodetector 320.

In this manner, according to the shape estimation device 10, the shape of each sensing part 410 is acquired by the arithmetic circuit 101. In addition, based on the acquired shape of the sensing part 410, the endoscope shape calculator 140 calculates the shape of the insertion section 812 of the endoscope 810. Thereby, the user can understand the shape (curvature or bend amount) of each sensing part 410 or the insertion section 812 while operating the endoscope 810. In addition, the endoscope controller 820 can properly control the operation of the endoscope 810 in accordance with the calculated shape of each sensing part 410 or the insertion section 812.

A description will be given of arithmetic operations which are executed by the arithmetic circuit 101 in the shape estimation device 10 of the present embodiment. To begin with, the information to be prepared in advance before using the shape estimation device 10 will be described. A light amount $D_{\lambda,n}$ of light of wavelength $\lambda n$, which is detected by the photodetector 320, is given by the following equation (1).

$$D_{\lambda,n} = E_{\lambda,n} \times A_{\lambda,n} \times B_{\lambda,n} \times L_{\lambda,n} \qquad \text{equation (1)}$$

Here, $E_{\lambda,n}$ is a light amount of light of wavelength $\lambda n$, which is emitted from the light source 310; $A_{\lambda,n}$ is an absorptivity of light of wavelength $\lambda n$ in the first optical absorber; $B_{\lambda,n}$ is an absorptivity of light of wavelength $\lambda n$ in the second optical absorber; and $L_{\lambda,n}$ is an absorptivity of light of wavelength $\lambda n$ by members other than the sensing parts 410, such as the optical branch 330, light guide 420 and reflector 430, which are included in an optical path along which light transmits in the sensor driver 300 and sensor unit 400.

The emission light amount $E_{\lambda,n}$ and absorptivity $L_{\lambda,n}$ do not depend on the shape of the sensing part 410. Accordingly, equation (1) representing the light amount $D_{\lambda,n}$ is rewritten as equation (2). Specifically, the light amount of light of wavelength $\lambda n$, which is detected by the photodetector 320 when each sensing part 410 is in a predetermined shape to be referenced (hereinafter referred to as "reference shape"), is calculated in advance as a reference light amount $I_{\lambda,n}$. Also, the ratio between the light amount of light of wavelength $\lambda n$, which is detected by the photodetector 320 when all sensing parts 410 (in this example, the second sensing part 412), other than the first sensing part 411, are in the reference shape, and the reference light amount $I_{\lambda,n}$, is set as a variation ratio $\alpha_{\lambda,n}$ in the first sensing part 411. Besides, the ratio between the light amount of light of wavelength $\lambda n$, which is detected by the photodetector 320 when all sensing parts 410 (in this example, the first sensing part 411), other than the second sensing part 412, are in the reference shape, and the reference light amount $I_{\lambda,n}$, is set as a variation ratio $\beta_{\lambda,n}$ in the second sensing part 412. Then, the light amount $D_{\lambda,n}$ is given by the following equation (2).

$$D_{\lambda,n} = I_{\lambda,n} \times \alpha_{\lambda,n} \times \beta_{\lambda,n} \qquad \text{equation (2)}$$

Now, the light absorptivity in the optical absorber 429 of each sensing part 410 varies in accordance with the shape of each sensing part 410, for example, curvature κ. Accordingly, the variation ratio $\alpha_{\lambda,n}$ in the first sensing part 411 is given by the following equation (3).

$$\alpha_{\lambda,n} = f_{\lambda,n}(\kappa_\alpha) \qquad \text{equation (3)}$$

Here, $\kappa_\alpha$ is the curvature of the first sensing part 411, and a function $f_{\lambda,n}$ is curvature characteristic information about the first sensing part 411.

Similarly, the variation ratio $\beta_{\lambda,n}$ in the second sensing part 411 is given by the following equation (4).

$$\beta_{\lambda,n} = g_{\lambda,n}(\kappa_\beta) \qquad \text{equation (4)}$$

Here, $\kappa_\beta$ is the curvature of the second sensing part 412, and a function $g_{\lambda,n}$ is curvature characteristic information about the second sensing part 412.

From equation (2), equation (3) and equation (4), the following equation (5) is obtained. In equation (5), the left side represents light amount information in an arbitrary shape, and the right side represents a light amount estimation value to be generated based on reference light amount information and curvature characteristic information.

$$D_{\lambda,n}(\kappa_\alpha, \kappa_\beta) = I_{\lambda,n} \times f_{\lambda,n}(\kappa_\alpha) \times g_{\lambda,n}(\kappa_\beta) \qquad \text{equation (5)}$$

For the reference shape for determining the reference light amount $I_{\lambda,n}$, for example, the case is adopted in which all of the sensing parts 410 are in the straight shape, that is, the case in which the curvature of each of the first sensing part 411 and second sensing part 412 is 0, and the radius of curvature thereof is ∞. However, the reference shape is not limited to this case, and the reference shape may be a shape other than the straight shape. The reference shape may not be the same shape with respect to all sensing parts 410, and arbitrary shapes may be set for the respective sensing parts 410. Hereinafter, a description will be given of the case in which the reference shape that is the straight shape is adopted for all sensing parts 410.

Figure 9:
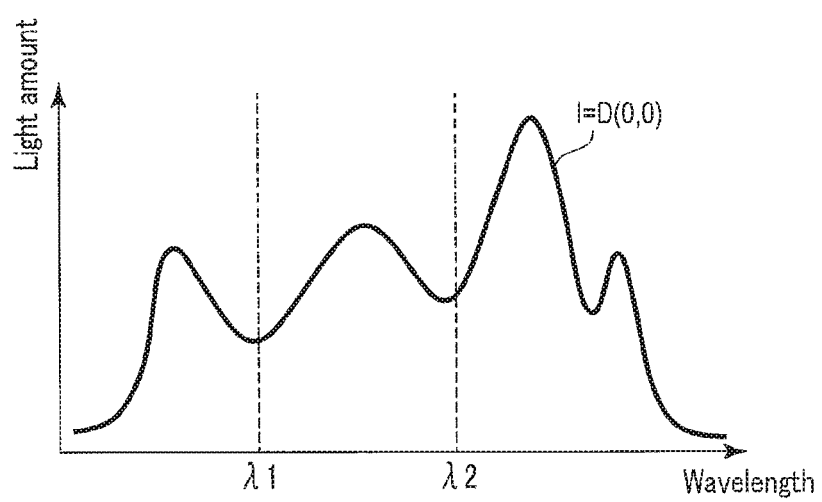
FIG. 9 is a graph showing an example of the relationship between wavelength and a reference light amount.

FIG. 9 is a graph showing an example of the relationship between wavelength and a reference light amount. A light amount $D_{\lambda n}$ (0,0) at a time when all sensing parts 410 are in the reference shape, that is, when $\kappa_\alpha=0$, and $\kappa_\beta=0$, is given by the following equation (6) by definition.

$$D_{\lambda n}(0,0)=I_{\lambda n} \qquad \text{equation (6)}$$

Specifically, by definition, the reference light amount is $I_{\lambda n}$, $f_{\lambda n}(0)=1$, and $g_{\lambda n}(0)=1$.

Figure 10:
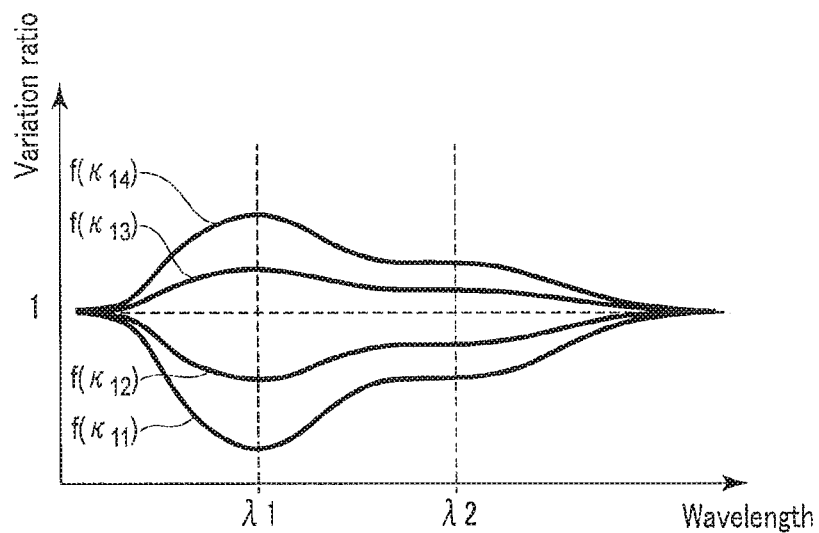
FIG. 10 is a graph showing an example of the relationship between wavelength and a variation ratio in light amount in a first sensing part.
Figure 11:
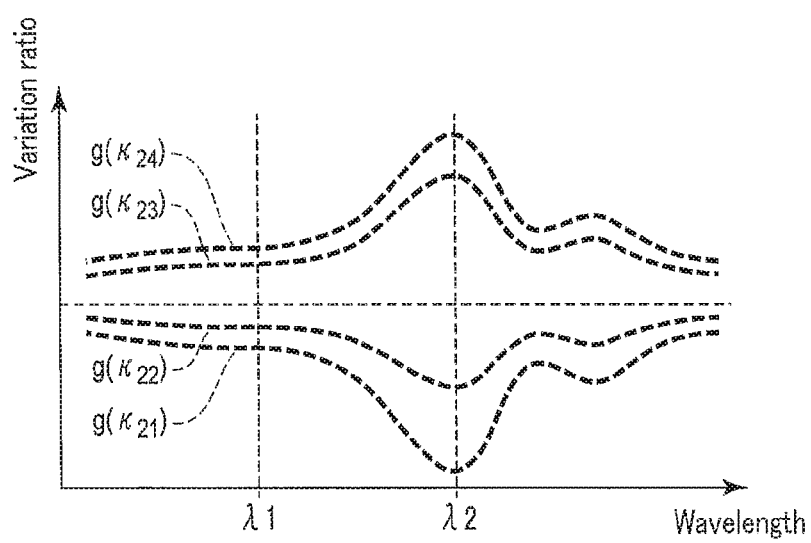
FIG. 11 is a graph showing an example of the relationship between wavelength and a variation ratio in light amount in a second sensing part.

The function $f_{\lambda n}$ and function $g_{\lambda n}$ being curvature characteristic information are obtained by varying, in a state in which the shapes of the sensing parts, other than a target sensing part, are set to be the reference shape, the curvature of the target sensing part within a possible range. FIG. 10 is a graph showing an example of the obtained curvature characteristic information $f_{\lambda n}(\kappa_\alpha)$. Here, the curvature $\kappa_\alpha$ is $\kappa_{11}<\kappa_{12}<\kappa_{13}<\kappa_{14}$. FIG. 11 is a graph showing an example of the obtained curvature characteristic information $g_{\lambda n}(\kappa_\beta)$. Here, the curvature $\kappa\beta$ is $\kappa_{21}<\kappa_{22}<\kappa_{23}<\kappa_{24}$. Each of FIG. 10 and FIG. 11 shows curvature characteristic information relating to four curvatures. However, the obtained curvature characteristic information is not limited to these, and the relationship between the wavelength and variation ratio in the emission wavelength range are obtained with respect to various curvatures.

Figure 12:
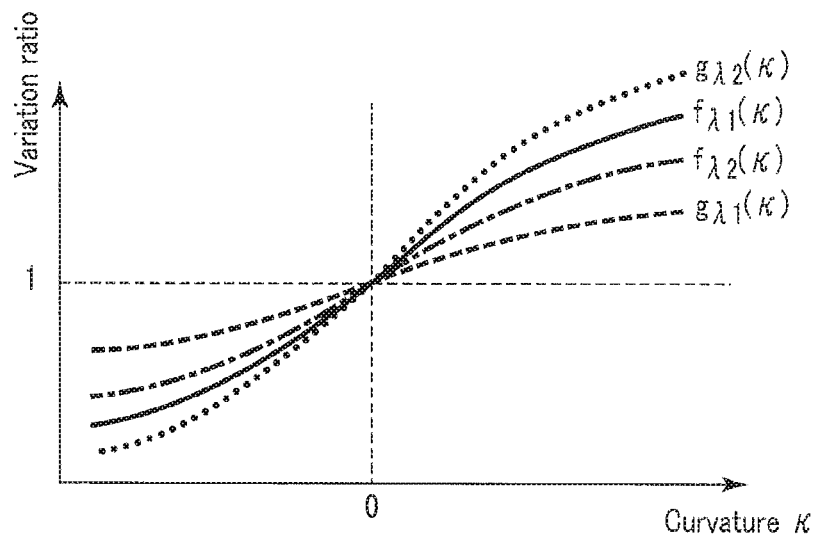
FIG. 12 is a graph showing an example of the relationship between the curvatures and variation ratios in light amount of the first sensing part and the second sensing part.

In this manner, the curvature characteristic information $f_{\lambda n}(\kappa_\alpha)$ of the first sensing part 411, which represents the relationship between the curvature $\kappa_\alpha$ and variation ratio $\alpha_{\lambda n}$, and the curvature characteristic information $g_{\lambda n}(\kappa_\beta)$ of the second sensing part 412, which represents the relationship between the curvature $\kappa_\beta$ and variation ratio $\beta_{\lambda n}$, are obtained. FIG. 12 is a graph showing an example of the thus obtained curvature characteristic information that is the relationship between the curvatures and variation ratios in the first sensing part 411 and the second sensing part 412.

From equation (5), the function $f_{\lambda n}(\kappa_\alpha)$ is given by the following equation (7).

$$f_{\lambda n}(\kappa_\alpha) = \frac{D_{\lambda n}(\kappa_\alpha, 0)}{I_{\lambda n}} \qquad \text{equation (7)}$$

Similarly, the function $g_{\lambda n}(\kappa_\beta)$ is given by the following equation (8).

$$g_{\lambda n}(\kappa_\beta) = \frac{D_{\lambda n}(0, \kappa_\beta)}{I_{\lambda n}} \qquad \text{equation (8)}$$

The curvature characteristic information and reference light amount information are acquired in advance, for example, when the endoscope system 1 is manufactured, or when the endoscope system 1 is installed, and are prestored in the storage circuit 120. The curvature characteristic information and reference light amount information may be acquired at each time of use.

Figure 13:
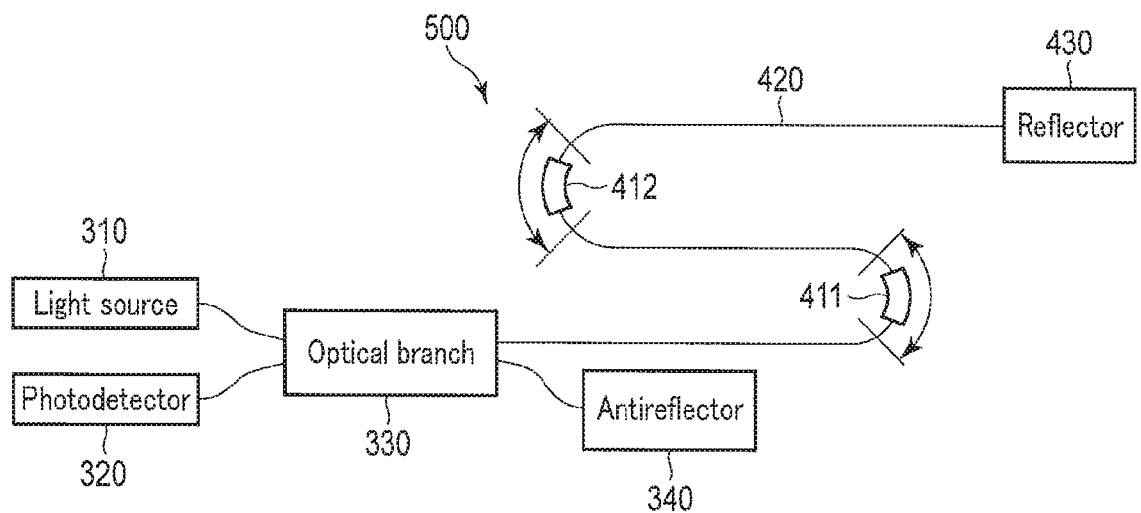
FIG. 13 is a view which schematically shows a state in which the first sensing part and the second sensing part bend at arbitrary curvatures.
Figure 14:
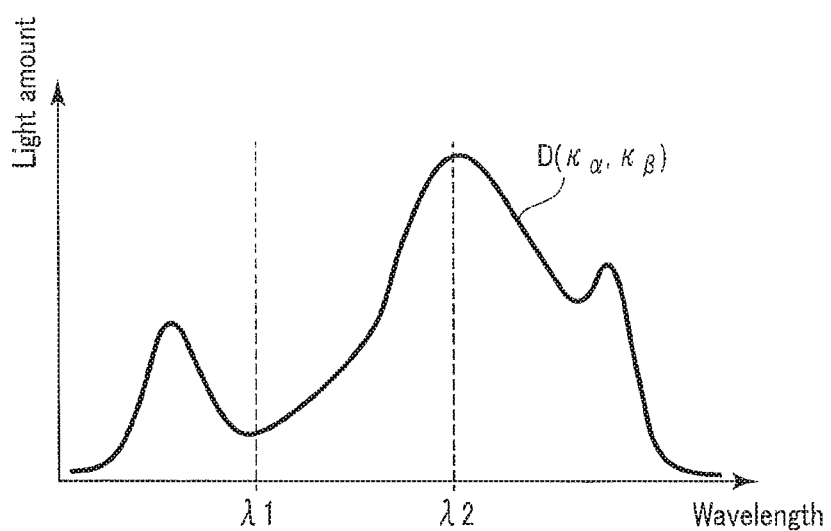
FIG. 14 is a graph showing an example of the relationship between wavelength and a light amount, which is obtained by the photodetector in the bend state of FIG. 13.

Next, arithmetic operations to be executed by the arithmetic circuit 101 at the time of using the shape estimation device 10 will be described. FIG. 13 is a view which schematically shows a state in which the first sensing part 411 and the second sensing part 412 of the sensor unit 400 bend at arbitrary curvatures $\kappa_\alpha$ and $\kappa_\beta$. FIG. 14 is a graph showing an example of the relationship between the wavelength and light amount, which is obtained by the photodetector 320 in the bend state of FIG. 13.

Figure 15:
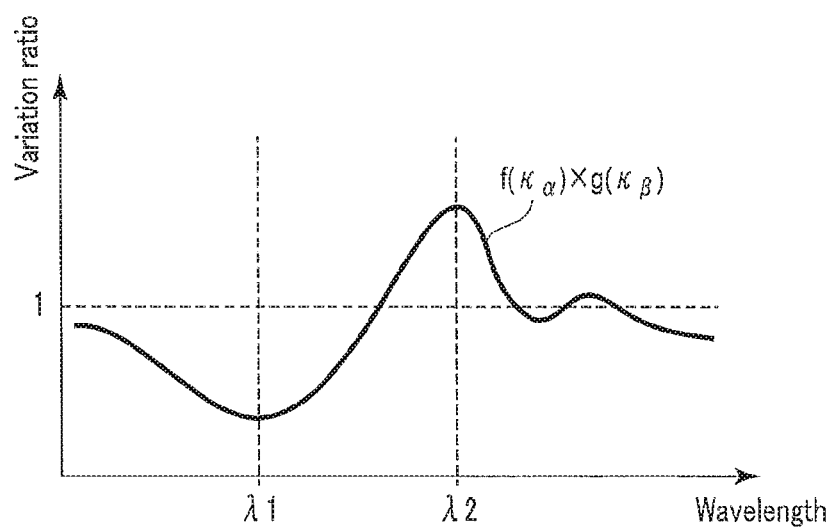
FIG. 15 is a graph showing an example of the relationship between wavelength, and a product between a variation ratio in light amount in the first sensing part and a variation ratio in light amount in the second sensing part.

From equation (5), the light amount D ($\kappa_\alpha$, $\kappa_\beta$) detected by the photodetector 320 is equal to a product between the pre-acquired reference light amount I shown in FIG. 9, on one hand, and a product $f(\kappa_\alpha) \times g(\kappa_\beta)$ of variation ratios of the first sensing part 411 and second sensing part 412, on the other hand. FIG. 15 is a graph showing an example of the product of variation ratios, that is, the relationship between the wavelength, and the product between the variation ratio in light amount in the first sensing part 411 and the variation ratio in light amount in the second sensing part 412.

Figure 16:
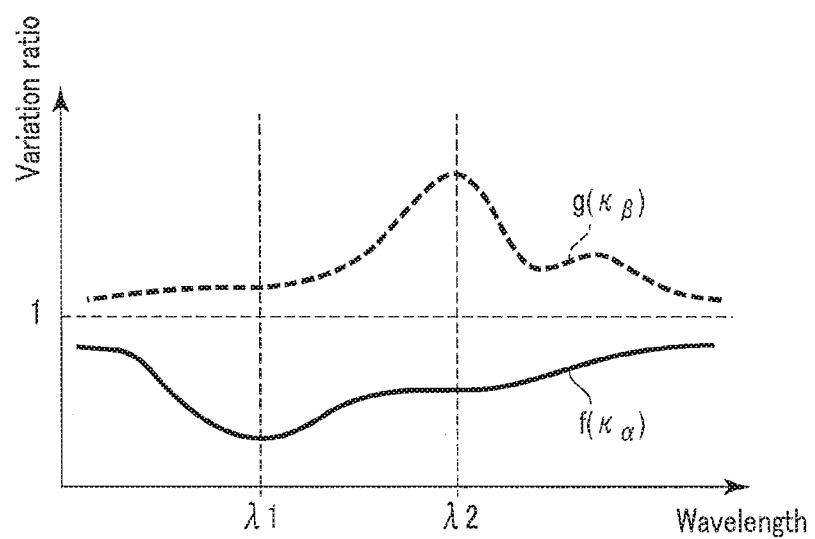
FIG. 16 is a graph showing an example of variation ratios of light amounts in the first sensing part and the second sensing part, the sensing parts being separated.

Here, the variation ratios in light amount in each sensing parts are independent from each other. Accordingly, if the product $f(\kappa_\alpha) \times g(\kappa_\beta)$ of variation ratios can be separated into the variation ratio $f(\kappa_\alpha)$ and $g(\kappa_\beta)$ of each sensing part 411 and 412, the respective curvatures $\kappa_\alpha$ and $\kappa_\beta$ can be found from the light amount D ($\kappa_\alpha$, $\kappa_\beta$). In other words, if each piece of curvature characteristic information can be calculated from the intermingled state of a plurality of pieces of curvature characteristic information being independent from each other, the shape in each sensing part can be calculated. FIG. 16 is a graph showing an example of the variation ratio $f(\kappa_\alpha)$ in light amount in the first sensing part 411 and the variation ratios $g(\kappa_\beta)$ in light amount in the second sensing part 412, the sensing parts being separated.

In the present embodiment, in order to calculate the curvature $\kappa_\alpha$ of the first sensing part 411 and the curvature $\kappa_\beta$ of the second sensing part 412, simultaneous equation expressed by the following equation (9) are solved, based on the light amounts $D_{\lambda 1}$ and $D_{\lambda 2}$ at a first wavelength $\lambda 1$ and a second wavelength $\lambda 2$ detected by the photodetector 320.

$$\begin{cases} D_{\lambda 1}(\kappa_\alpha, \kappa_\beta) = I_{\lambda 1} \times f_{\lambda 1}(\kappa_\alpha) \times g_{\lambda 1}(\kappa_\beta) \\ D_{\lambda 2}(\kappa_\alpha, \kappa_\beta) = I_{\lambda 2} \times f_{\lambda 2}(\kappa_\alpha) \times g_{\lambda 2}(\kappa_\beta) \end{cases} \qquad \text{equation (9)}$$

The reference light amounts $I_{\lambda 1}$ and $I_{\lambda 2}$ and the curvature characteristic information $f_{\lambda 1}$, $f_{\lambda 2}$, $g_{\lambda 1}$, and $g_{\lambda 2}$ are pre-acquired and stored in the storage circuit 120 as described above. Accordingly, based on the light amounts $D_{\lambda 1}$ and $D_{\lambda 2}$, the curvature $\kappa_\alpha$ of the first sensing part and the curvature $\kappa_\beta$ of the second sensing part 412 can be calculated. In other words, the shape of each sensing part is found by calculating the light amount estimation value, based on the light amount estimation relationship expressed by the above-described function form. The light amount estimation relationship is not limited to the relationship expressed by the above-described function form, and may be a light amount estimation relationship expressed by a table (lookup table) in which the relationship between the wavelength and light amount is stored.

Although the curvature is set as the parameter representing the shape of each sensing part, and the shape estimation arithmetic operation using the curvature characteristic information was described, the parameter is not limited to the curvature. For example, it is possible to adopt some other parameter, such as a radius of curvature, which represents the shape of each sensing part, and a shape estimation arithmetic operation using the curvature characteristic information corresponding to that parameter.

Figure 17:
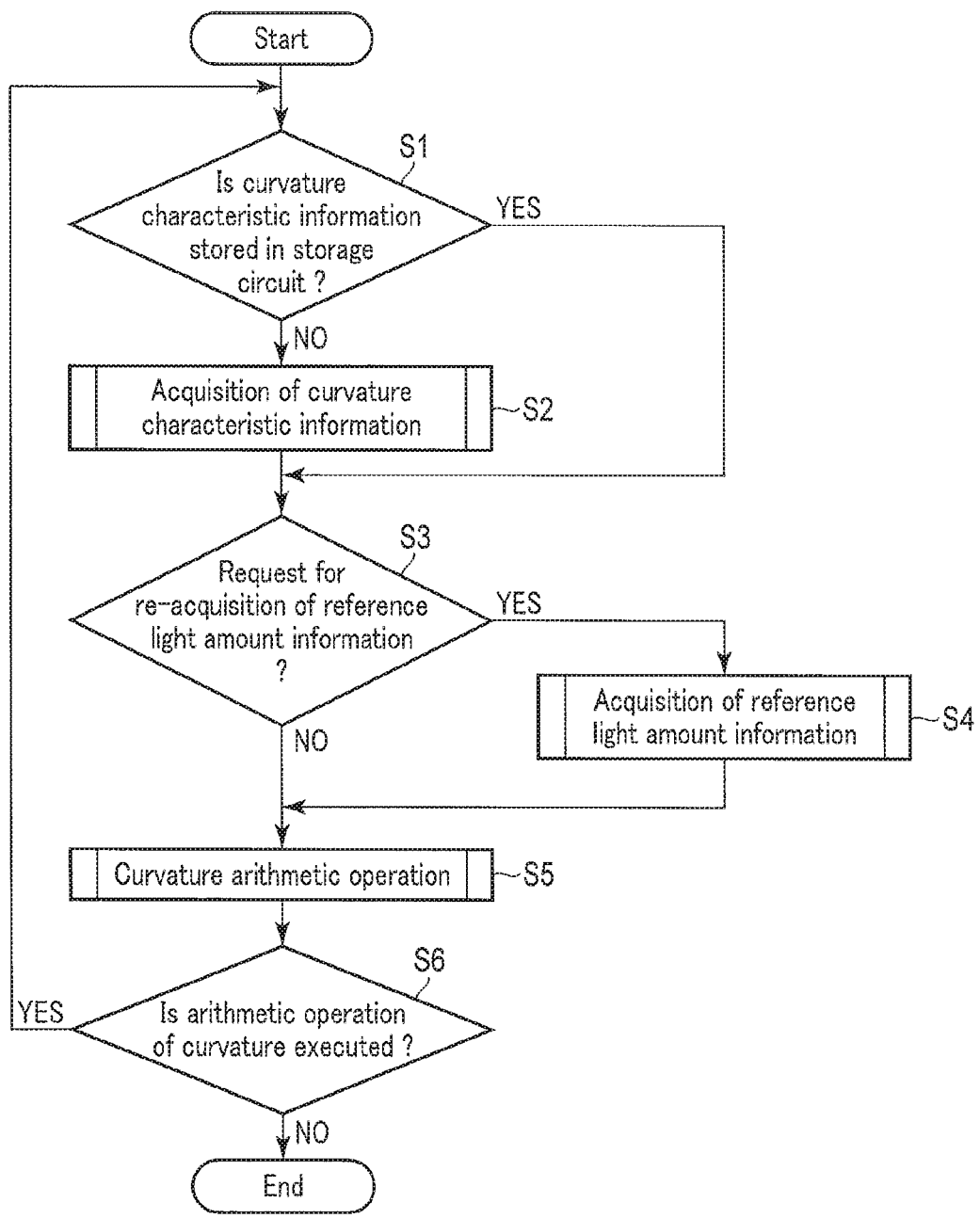
FIG. 17 is a flowchart showing the flow of a process in a controller.

FIG. 17 is a flowchart showing the flow of a process in the controller 100. In step S1, the controller 100 determines whether curvature characteristic information is stored in the storage circuit 120 or not. If it is determined that the curvature characteristic information is not stored (NO), the process advances to step S2, and the controller 100 acquires the curvature characteristic information.

Figure 18:
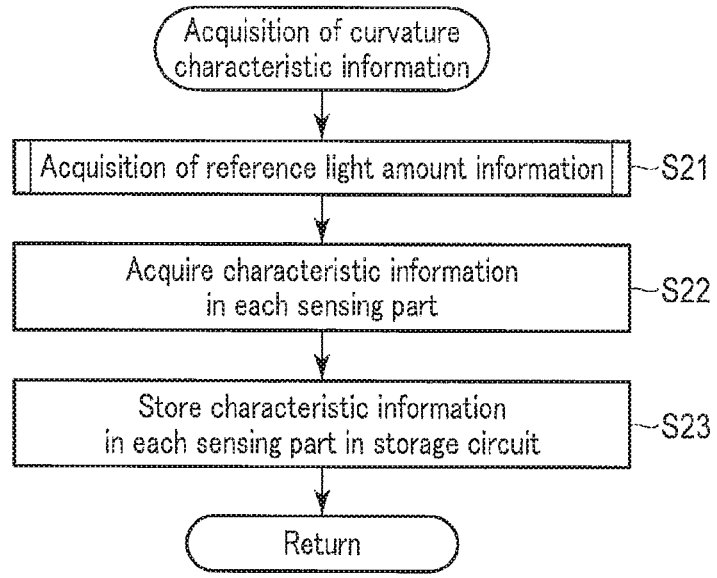
FIG. 18 is a flowchart showing an example of acquisition of curvature characteristic information.

FIG. 18 is a flowchart showing an example of acquisition of the curvature characteristic information. In step S21, the controller 100 acquires reference light amount information $I_\lambda$.

Figure 19:
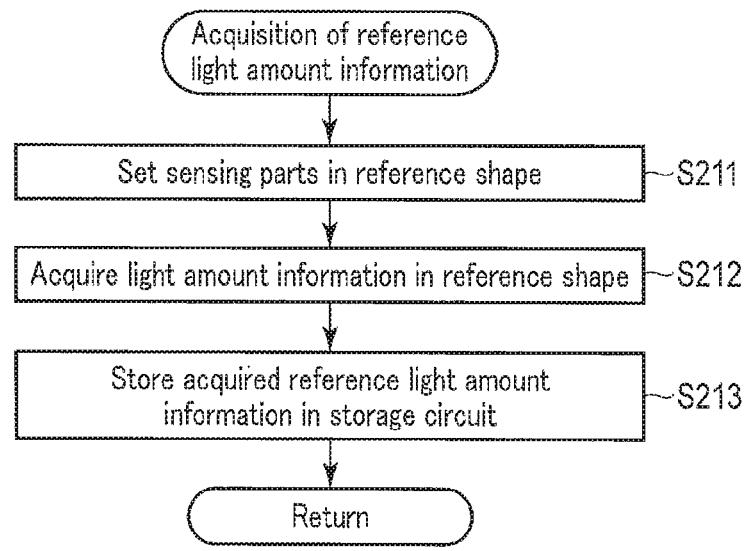
FIG. 19 is a flowchart showing an example of acquisition of reference light amount information.

FIG. 19 is a flowchart showing an example of acquisition of the reference light amount information. In step S211, the controller 100 sets the sensing parts 410 in the reference shape. In the present embodiment, the controller 100 sets all sensing parts 410 in the straight shape. In the case that all sensing parts 410 are manually set in the reference shape, the controller 100 confirms in step S211 whether all sensing parts 410 are set in the reference shape. In step S212, the controller 100 acquires light amount information $I_\lambda$ in the reference shape (equation (6)). In step S213, the acquired light amount information $I_\lambda$ is stored in the storage circuit 120. Then, the acquisition of the light amount information $I_\lambda$ is completed, and the process advances to step S22.

Referring back to FIG. 18, in step S22, the controller 100 acquires curvature characteristic information on each sensing part 410. Specifically, in the present embodiment, the controller 100 acquires curvature characteristic information $f_{\lambda,n}(\kappa_\alpha)$ on the first sensing part 411 and curvature characteristic information $g_{\lambda,n}(\kappa_\beta)$ on the second sensing part 412 (equation (7) and equation (8)). Further, in step S23, the acquired curvature characteristic information is stored in the storage circuit 120. Thus, the acquisition of the curvature characteristic information is completed.

Referring back to FIG. 17, after the acquisition of the curvature characteristic information in step S2, or alternatively if it is determined in step S1 that the curvature characteristic information is stored in the storage circuit 120 (YES), the process goes to step S3. The case in which "YES" is determined in step S1 is, for example, a case in which the acquisition of the curvature characteristic information was made at a time of the factory shipment of the endoscope system 1 or at a time of installation of the endoscope system 1.

In step S3, the controller 100 determines whether there is a request for re-acquisition of the reference light amount information. If it is determined that there is the request (YES), the process advances to step S4. Then, in step S4, the controller 100 acquires the reference light amount information by the above-described subroutine (steps S211 to S213) of the acquisition of reference light amount information. The case in which such a request for re-acquisition is made is, for example, a case in which a connection to a controller, which is different from the above-described controller 100, was made, or a case in which the sensor driver 300 and the sensor unit 400 were disconnected and reconnected.

After the acquisition of the reference light amount information $I_\lambda$ in step S4, or if it is determined in step S3 that the request is not present (NO), the process advances to step S5, and the arithmetic circuit 101 of the controller 100 executes curvature arithmetic operations of the respective sensing parts 410.

FIG. 20 is a flowchart showing an example of a curvature arithmetic process. In step S51, the shape arithmetic circuit 110 reads out the reference light amount information $I_\lambda$ and curvature characteristic information $f_{\lambda,n}(\kappa_\alpha)$, $g_{\lambda,n}(\kappa_B)$, from the storage circuit 120. Then, in step S52, the shape arithmetic circuit 110 acquires light amount information $D_{\lambda,n}$ in an arbitrary shape by the photodetector 320 via the input circuit 130. Further, in step S53, the shape arithmetic circuit 110 calculates the respective curvatures $\kappa_\alpha$ and $\kappa_\beta$ from the light amount information $D_{\lambda,n}$, reference light amount information $I_\lambda$ and curvature characteristic information $f_{\lambda,n}(\kappa_\alpha)$, $g_{\lambda,n}(\kappa_B)$ in the manner as described above (equation (9)).

Then, in step S54, the shape arithmetic circuit 110 transmits each of the calculated curvatures $\kappa_\alpha$ and $\kappa_\beta$ to the output circuit 160. Thus, the curvature arithmetic operations are completed.

Referring back to FIG. 17, after the curvature arithmetic process in step S5, the process advances to step S6. In step S6, the controller 100 determines whether or not to execute the arithmetic operations of curvatures. If it is determined that the arithmetic operations of curvatures are executed (YES), the process returns to step S1, and the process of step S1 onwards is repeated. If it is determined that the arithmetic operations of curvatures are not executed (NO), the process terminates.

The curvature characteristics depend on only the absorption characteristics of the optical absorbers 429 of the sensing parts 410, and do not depend on the characteristics of the light source 310 or photodetector 320. Accordingly, it is possible to separate the respective structural components of the sensor driver 300, and to use, for example, a light source which emits light of a predetermined emission wavelength region, or a photodetector having detection sensitivity over all wavelengths which the controller 100 requires. In other words, curvature characteristics can be acquired by some other light source or photodetector, and replacement with some other sensor driver is possible.

According to the present embodiment, the light guide 420 being a constituent of the sensor unit 400 is provided with the plurality of sensing parts 410. In order to estimate the shape of each of these sensing parts 410, wavelengths, the number of which is greater than the number of sensing parts 410, are used. The light amount information of each of these wavelengths in each of sensing parts 410 is detected by the photodetector 320 of the sensor driver 300. Then, the shape of the sensing part 410 or the insertion section 812 of the endoscope 810 is estimated, based on the detected light amount information, and the light amount estimation value calculated based on the light amount estimation relationship which includes the shape characteristic information and is prestored in the storage circuit 120. In this manner, according to the present embodiment, there can be provided a shape estimation device being able to estimate a shape.

Additionally, according to the present embodiment, variation ratios of light in the sensing parts 410 are used in order to calculate the curvature. Therefore, the curvature arithmetic operation can be executed without depending on the spectrum of the light source 310 of the sensor driver 300 and the spectral sensitivity of the photodetector 320.

Additionally, according to the present embodiment, no information of the distance between the light source 310 and the sensing parts 410 provided on the light guide 420 is needed for the curvature arithmetic operation. Therefore, the curvature arithmetic operation can be executed without taking into account the positional relationship between the light source 310 and the sensing parts 410.

Additionally, according to the present embodiment, the light absorption and loss by the optical branch 330 of the sensor driver 300 or by the reflector 430 of the sensor unit 400 are constant without depending on the bend amount of the sensing parts 410. Accordingly, the reference light amount information is calculated in the state in which the loss is included. Therefore, the calculation can be made without giving additional consideration to the influence of the optical branch 330 and the reflector 430.

The first embodiment may also be implemented in the following modes.

(First Mode)

The request for re-acquisition of the reference light amount information, which is determined in step S3, occurs, for example, in a case in which the optical branch 330 of the sensor driver 300 and the light guide 420 of the sensor unit 400 were disconnected and reconnected. The controller 100 may be configured to determine, in such a case, whether the connection is maintained, that is, whether the disconnection and reconnection have been made.

(Second Mode)

Figure 21:
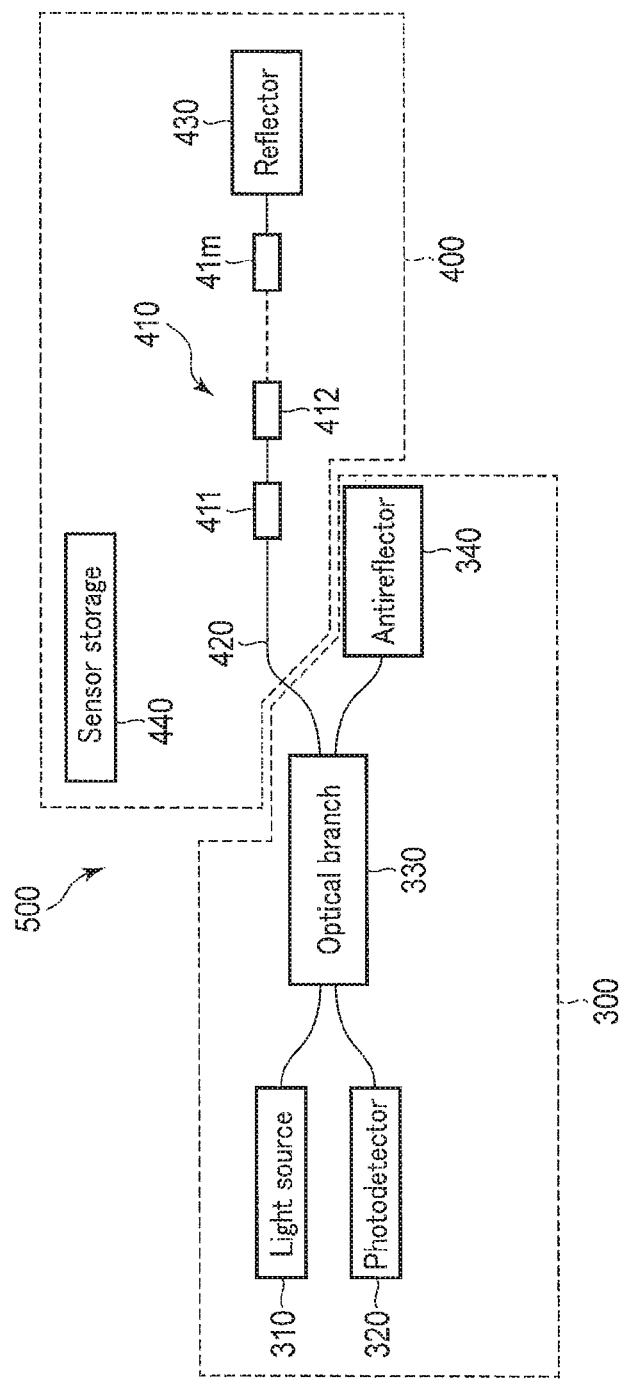
FIG. 21 is a block diagram showing an example of the configuration of the sensor.

FIG. 21 is a block diagram showing an example of the configuration of the sensor 500. In the present mode, the sensor unit 400 includes a sensor storage 440. In the sensor storage 440, sensor identification information and curvature characteristic information are prestored, for example, at a time of factory shipment or at a time of device installation. The sensor identification information, which is so-called ID information, is information for identifying the kind or individual of the sensor unit 400, and should preferably be unique. Also in the acquisition of the curvature characteristic information, the curvature characteristic information is stored in the sensor storage 440 in step S213 of FIG. 19.

In addition, when a connection was made to some other controller (when no curvature characteristic information exists in the storage circuit 120), instead of acquiring the curvature characteristic information in step S2 of FIG. 17, the curvature characteristic information is read out of the sensor storage 440. Thereby, even when the sensor driver 300 was connected to some other controller, there is no need to re-acquire the curvature characteristics.

In an environment in which a plurality of sensor units are used, a step, in which the controller 100 confirms the sensor identification information of the connected sensor unit 400, may be provided prior to step S1 immediately after the start of the flow of FIG. 17. In this case, it is presupposed that the curvature characteristic information and sensor identification information are associated, and the curvature characteristic information (curvature characteristic information of each of sensor units) is stored in the storage circuit 120.

In the step of confirming the sensor identification information, for example, the sensor identification information is input from the input circuit 130 by the input device 190. The sensor identification information may be imprinted on or attached to the sensor unit 400, or may be stored in a tag. Preferably, the tag should be a non-contact tag such as an RF-ID. Alternatively, the sensor identification information may be stored in the above-described sensor storage 440 and may be read therefrom, or information stored in some other storage medium may be read out. In addition, in the case of sensor identification information which fails to meet the above presupposition and is not stored in the storage circuit 120, a process may be executed according to the flow of FIG. 17.

According to the second mode, the curvature characteristic information can be extracted from the sensor identification information. Thus, even when a connection was made to some other sensor unit, the curvature characteristic information can be extracted from the sensor identification information. Therefore, there is no need to re-acquire the curvature characteristics.

(Third Mode)

Equation (9) may be expressed as the following equation (10) by taking logarithms.

$$\begin{cases} \log D_{\lambda 1}(\kappa_\alpha, \kappa_\beta) = \log I_{\lambda 1} + \log f_{\lambda 1}(\kappa_\alpha) + \log g_{\lambda 1}(\kappa_\beta) \\ \log D_{\lambda 2}(\kappa_\alpha, \kappa_\beta) = \log I_{\lambda 2} + \log f_{\lambda 2}(\kappa_\alpha) + \log g_{\lambda 2}(\kappa_\beta) \end{cases} \quad \text{equation (10)}$$

By taking logarithms, the right side of equation (9) is expressed by addition. Then, it can be thought that the logarithm of the variation ratio of each sensing part 410 is an absorbance with reference to the reference light amount information. The curvature characteristic information of the first sensing part 411 and the curvature characteristic information of the second sensing part 412 are given by the following equation (11) and equation (12) by taking logarithms of equation (3) and equation (4).

$$F_{\lambda,n}(\kappa_\alpha) = \log f_{\lambda,n}(\kappa_\alpha) \quad \text{equation (11)}$$

$$G_{\lambda,n}(\kappa_\beta) = \log g_{\lambda,n}(\kappa_\beta) \quad \text{equation (12)}$$

FIG. 22 is a graph showing an example of the curvature characteristic information which is the relationship between the curvature and light absorbance of the first sensing part 411 and the second sensing part 412 in the case where logarithms were taken as described above. From equation (10), equation (11) and equation (12), the following equation (13) is obtained.

$$\begin{cases} \log D_{\lambda 1}(\kappa_\alpha, \kappa_\beta) = \log I_{\lambda 1} + F_{\lambda 1}(\kappa_\alpha) + G_{\lambda 1}(\kappa_\beta) \\ \log D_{\lambda 2}(\kappa_\alpha, \kappa_\beta) = \log I_{\lambda 2} + F_{\lambda 2}(\kappa_\alpha) + G_{\lambda 2}(\kappa_\beta) \end{cases} \quad \text{equation (13)}$$

According to the third mode, since the product of variation ratios of the respective sensing parts 410 can be rewritten as the sum of variation ratios of the respective sensing parts, the calculation can be made easier.

(Fourth Mode)

FIG. 23 is a graph showing an example of the relationship between the light wavelengths and absorptivities in the first optical absorber and the second optical absorber. The wavelengths to be used for the calculation of the shape are not limited to specific wavelengths λ1 and λ2, and may be a first wavelength band $d_{\lambda 1}$ and a second wavelength band $d_{\lambda 2}$, each having a band width as shown in FIG. 23. For example, the first sensing part 411 and the second sensing part 412 include wavelength bands (characteristic absorption bands), the wavelength bands is a wavelength range of mutual absorption (that is, the wavelength range in which the first optical absorber and the second optical absorber have absorptivities) and a wavelength range of different absorption wavelength characteristics (that is, a wavelength range in which the first optical absorber and the second optical absorber differ in absorptivities from each other). The number of wavelength bands is equal to or larger than that of sensing parts (that is, two or more wavelength bands).

According to the present mode, the wavelength, which is used for the calculation of the shape, is not a specific single wavelength, but has a band width. Thus, there is no need to increase the wavelength resolution of the photodetector 320. Accordingly, the cost of the photodetector 320 can be reduced. In addition, since it is not that only local wavelengths are used, the robustness to noise is enhanced.

The wavelength band to be used may include a part of the other wavelength band. For example, the first wavelength band and second wavelength band may overlap. Since pieces of curvature characteristic information of the respective sensing parts are independent from each other, the curvature of each sensing part can be calculated, even if one wavelength band includes a part of the other wavelength band.

(Fifth Mode)

FIG. 24 is a block diagram showing an example of the configuration of the sensor driver 300 and sensor unit 400.

The sensor driver 300 includes a light source 310 and a photodetector 320. The sensor unit 400 includes a light guide 420 provided with a plurality of sensing parts 410. The above-described optical branch 330, antireflector 340 and reflector 430 are not provided. The light source 310 is optically connected to a proximal end of the light guide 420. The photodetector 320 is optically connected to a distal end of the light guide 420. Light emitted from the light source 310 is guided in the light guide 420. The guided light transmits in the light guide 420 from the proximal-end side to the distal-end side, and reaches the photodetector 320.

According to the mode in which the optical branch, antireflector and reflector are not provided, the loss of light due to these components can be decreased. Therefore, the light amount of the light source can be decreased.

(Sixth Mode)

The photodetector 320 may be configured to be capable of detecting the light amounts $D_{\lambda 1}$ and $D_{\lambda 2}$ at a plurality of predetermined wavelengths $\lambda 1$ and $\lambda 2$, or wavelength bands $d_{\lambda 1}$ and $d_{\lambda 2}$. For example, the wavelength characteristics of the emission intensity of light guided into the guide light 420 are varied at a time instant, and the light amount at that time instant is detected.

Figure 26:
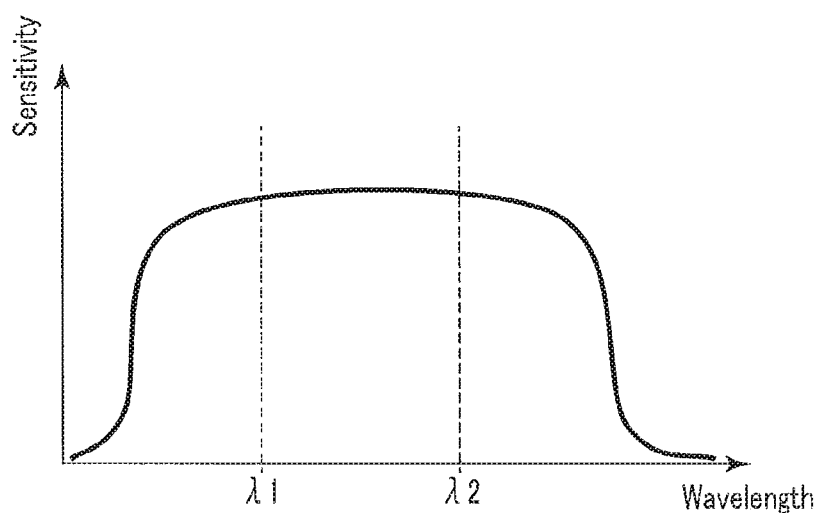
FIG. 26 is a graph showing an example of the relationship between wavelength of light, which is falls on the photodetector, and detection sensitivity of the photodetector, the relationship corresponding to FIG. 25.

FIG. 25 is a graph showing an example of the relationship between the wavelength and the light emission intensity of the light source at time instants t1 and t2. In FIG. 25, the relationship at time instant t1 is indicated by a solid line, and the relationship at time instant t2 is indicated by a broken line. The light source 310 emits, by a filter or the like, light having a peak at wavelength $\lambda 1$ at time instant t1, and light having a peak at wavelength $\lambda 2$ at time instant t2. FIG. 26 is a graph showing an example of the relationship between the wavelength of light, which falls on the photodetector, and the detection sensitivity of the photodetector, the relationship corresponding to FIG. 25. The photodetector 320 includes a light receiving element (a light receiving element which does not have a spectral function by a filter or the like) having detection sensitivity to the intensity of light having peaks at the wavelengths $\lambda 1$ and $\lambda 2$.

According to the sixth embodiment, by detecting the light amounts from the light receiving element in synchronism with the time instants t1 and t2, the light amount information (detected light amount at each wavelength band) can be obtained.

(Variant)

Hereinafter, as a variant of the first embodiment, a description will be given of a curvature arithmetic operation in a case in which a third sensing part is provided in addition to the first sensing part and second sensing part, that is, in a case in which the number of sensing parts is three. An optical absorber provided in the third sensing part is referred to as "third optical absorber".

Figure 27:
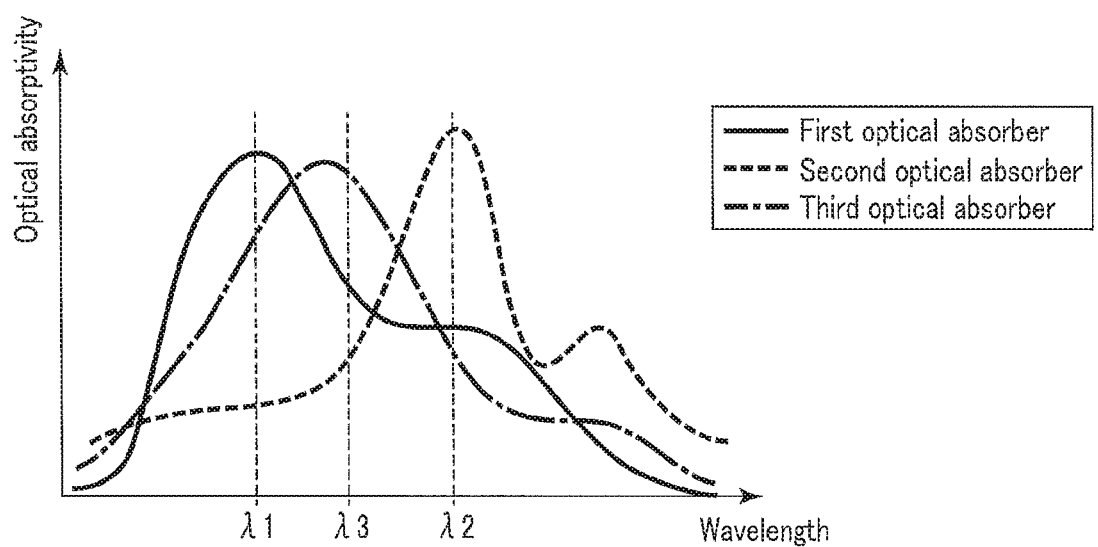
FIG. 27 is a graph showing an example of the relationship between light wavelengths and absorptivities in first to third optical absorbers.

FIG. 27 is a graph showing an example of the relationship between the light wavelengths and absorptivities in the first optical absorber, second optical absorber and third optical absorber. Since the first optical absorber and second optical absorber are the same as in FIG. 7, a description thereof is omitted. In FIG. 27, a one-dot-and-dash line indicates light absorption characteristics of the third optical absorber. A third wavelength $\lambda 3$ is a characteristic wavelength of a spectrum which the third optical absorber absorbs. The characteristic wavelength is, for example, a wavelength at which absorption becomes maximum. The light absorption characteristics of the third optical absorber are different from the light absorption characteristics of the first optical absorber and second optical absorber.

A variation ratio $\gamma_{\lambda,n}$ in the third sensing part, like the variation ratios of the other sensing parts, is given by the following equation (14).

$$\gamma_{\lambda,n} = h_{\lambda,n}(\kappa_\gamma) \quad \text{equation (14)}$$

Here, $\kappa_\gamma$ is the curvature of the third sensing part, and a function $h_{\lambda,n}$ is curvature characteristic information about the third sensing part. For example, a case in which all the three sensing parts are in the straight shape is adopted for the reference shape. It is assumed that the wavelengths, which are used for arithmetic operations, are characteristic wavelengths $\lambda 1$, $\lambda 2$ and $\lambda 3$, which are absorbed by the respective sensing parts.

By rewriting equation (9) as equation (15), the curvatures $\kappa_\alpha$, $\kappa_\beta$ and $\kappa_\gamma$ of the respective sensing parts can be calculated.

$$\begin{cases} D_{\lambda 1}(\kappa_\alpha, \kappa_\beta, \kappa_\gamma) = I_{\lambda 1} \times f_{\lambda 1}(\kappa_\alpha) \times g_{\lambda 1}(\kappa_\beta) \times h_{\lambda 1}(\kappa_\gamma) \\ D_{\lambda 2}(\kappa_\alpha, \kappa_\beta, \kappa_\gamma) = I_{\lambda 2} \times f_{\lambda 2}(\kappa_\alpha) \times g_{\lambda 2}(\kappa_\beta) \times h_{\lambda 2}(\kappa_\gamma) \\ D_{\lambda 3}(\kappa_\alpha, \kappa_\beta, \kappa_\gamma) = I_{\lambda 3} \times f_{\lambda 3}(\kappa_\alpha) \times g_{\lambda 3}(\kappa_\beta) \times h_{\lambda 3}(\kappa_\gamma) \end{cases} \quad \text{equation (15)}$$

Even in the case where the number of sensing parts is four or more, the curvatures of the respective sensing parts can similarly be calculated.

Second Embodiment

A second embodiment of the present invention will be described with reference to FIG. 28 and FIG. 29. Hereinafter, a description of the parts common to the first embodiment is omitted, and only different parts are described.

Figure 28:
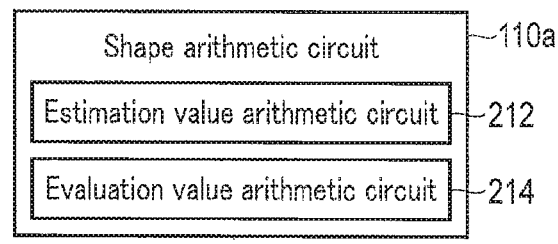
FIG. 28 is a block diagram showing an example of a shape arithmetic circuit in a second embodiment.
Figure 29:
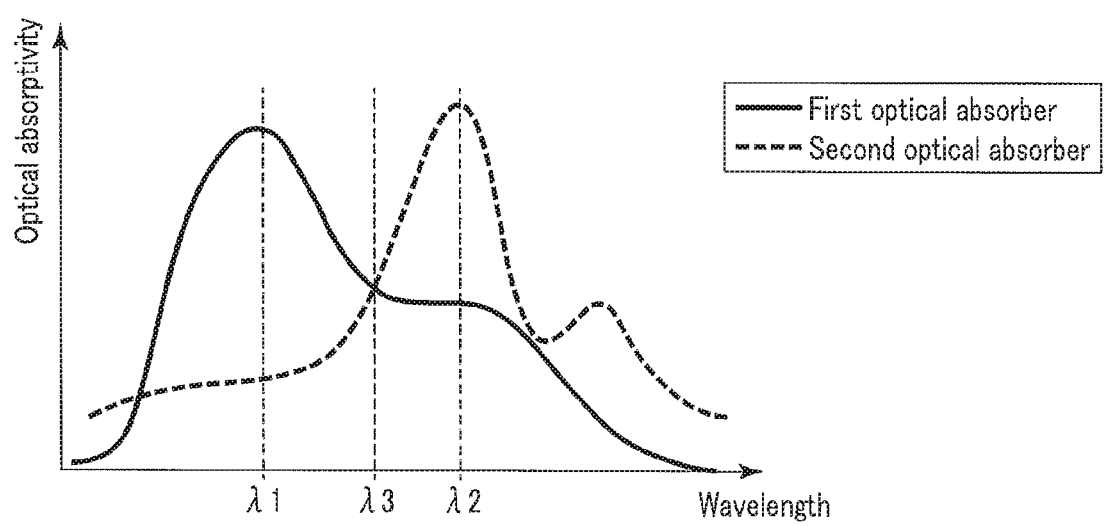
FIG. 29 is a graph showing an example of the relationship between light wavelengths and absorptivities in the first optical absorber and the second optical absorber.

FIG. 28 is a block diagram showing an example of a shape arithmetic circuit 110a in the second embodiment. The shape arithmetic circuit 110a includes the estimation value arithmetic circuit 212, and an evaluation value arithmetic circuit 214 being a shape optimizing circuit. The evaluation value arithmetic circuit 214 executes an arithmetic operation for optimizing the shape of each sensing part 410, as will be described below.

In the second embodiment, the relationship between light wavelengths and absorptivities in the first optical absorber and second optical absorber, which is the same as in the first embodiment, is utilized. Furthermore, the curvature of each sensing part 410 is estimated by using the detected light amount information $D_{\lambda,3}$, reference light amount information $I_{\lambda,3}$, and variation ratios $f_{\lambda,3}$ and $g_{\lambda,3}$ of the respective sensing parts at the third wavelength $\lambda 3$. FIG. 29 is a graph showing an example of the relationship between the light wavelengths and absorptivities in the first optical absorber and the second optical absorber in the second embodiment.

To begin with, a difference $\Delta_{\lambda,n}$ between the right side and left side in equation (9) is calculated (n=1, 2, 3). Specifically, the following equation (16) represents the difference between the value of light amount information and the estimation light amount value in an arbitrary shape.

$$\Delta_{\lambda,n} = D_{\lambda,n}(\kappa_\alpha, \kappa_\beta) - I_{\lambda,n} \times f_{\lambda,n}(\kappa_\alpha) \times g_{\lambda,n}(\kappa_\beta) \quad \text{equation (16)}$$

In the present embodiment, in step S53 of the flow shown in FIG. 20, the evaluation value arithmetic circuit 214 optimizes the curvature of each sensing part 410 such that the difference between the value of light amount information and the estimated light amount information decreases. For example, an evaluation value J, which is the sum of squares of differences $\Delta_{\lambda,n}$ at respective wavelengths, is calculated, and the curvature of each sensing part 410 is determined such that the evaluation value J becomes minimum. The evaluation value J is given by the following equation (17).

$$J = \sum (\Delta_{\lambda n})^2 = \Delta_{\lambda 1}^2 + \Delta_{\lambda 2}^2 + \Delta_{\lambda 3}^2 \quad \text{equation (17)}$$

For example, as indicated by the following equation (18), the degree of contribution to the evaluation value J at each wavelength or wavelength band may be adjusted by giving a weighting factor $w_n$.

$$J = \sum w_n(\Delta_{\lambda n})^2 = w_1\Delta_{\lambda 1}^2 + w_2\Delta_{\lambda 2}^2 + w_3\Delta_{\lambda 3}^2 \quad \text{equation (18)}$$

In the setting of the weighting factor $w_n$, for example, it is better to increase the degree of contribution of such a wavelength or wavelength band that the light absorption amount of the optical absorber of each sensing part 410 becomes maximum.

According to the present embodiment, the evaluation value arithmetic circuit 214 as the shape optimizing circuit executes the arithmetic operation for optimization, and thereby the shape of each sensing part 410 can be calculated with higher precision. In addition, it is possible to provide a shape estimation device which has redundancy and is robust to an effect such as noise.

Now, the endoscope has been taken as an example of the device to which the shape estimation device is applied, and the endoscope system has been described. However, the object into which the shape estimation device is incorporated is not limited to the endoscope, and the shape estimation device is applicable to a catheter which is inserted into an insertion target, a surgery-assisting robot, etc.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A shape estimation device comprising:
a sensor including a plurality of sensing parts disposed to be spaced apart from each other, the plurality of sensing parts each having a different light absorptivity at a respective wavelength, the sensor being configured such that a light amount to be detected by each of the plurality of sensing parts varies in accordance with a change in a bend shape of each of the plurality of sensing parts; and
a controller comprising hardware, the controller being configured to:
receive light amount information which is a relationship between the wavelength and the light amount acquired from each of the plurality of sensing parts;
store a light amount estimation relationship including shape characteristic information representing a relationship between the light amount and a shape of each of the plurality of sensing parts with respect to each of the plurality of sensing parts; and
calculate the shape of each of the plurality of sensing parts, with respect to the light amount information detected from the plurality of sensing parts, using the light amount information of the shape characteristic information wherein the sensor includes a light source a light guide including the plurality of sensing parts which are provided with optical materials having optical modulation characteristics being different from each other, the light guide being configured to guide light emitted from the light source; and a photodetector configured to detect light amount information of each of a plurality of wavelength bands of the light guided in the light guide.

2. The shape estimation device according to claim 1, wherein pieces of the shape characteristic information are independent from each other, and
an arithmetic operation of the shape of each of the plurality of sensing parts comprises calculating each of the pieces of the shape characteristic information, based on each of a plurality of pieces of the light amount information and each of the light amount estimation values which are different from each other.

3. The shape estimation device according to claim 2, wherein the light amount estimation relationship includes reference light amount information, and
the reference light amount information is the light amount information acquired in a state in which the plurality of sensing parts are set in a predetermined reference shape.

4. The shape estimation device according to claim 3, wherein the predetermined reference shape is a state in which all of the plurality of sensing parts are set in a straight shape.

5. The shape estimation device according to claim 3, wherein the shape characteristic information of each of the sensing parts is the light amount information acquired in a state in which the plurality of sensing parts, excluding a sensing part that is a target of acquisition of the shape characteristic information, are set in the predetermined reference shape.

6. The shape estimation device according to claim 3, wherein the shape characteristic information is a variation ratio of the light amount in relation to the reference light amount information.

7. The shape estimation device according to claim 3, wherein the shape characteristic information is an absorbance of the light amount in relation to the reference light amount information.

8. The shape estimation device according to claim 1, wherein the optical modulation characteristics are at least light absorption characteristics.

9. The shape estimation device according to claim 8, wherein the optical materials have different optical modulation characteristics which are light absorptivities at respective wavelengths in each of the plurality of wavelength bands.

10. The shape estimation device according to claim 1, wherein a number of the wavelength bands is equal to or greater than a number of the sensing parts.

11. The shape estimation device according to claim 1, wherein each of the plurality of wavelength bands includes a part of the other of the plurality of wavelength bands.

12. The shape estimation device according to claim 1, wherein the sensor is configured to provide sensor identification information to the controller to identify the sensor.

13. The shape estimation device according to claim 12, wherein controller is configured to associate and store the sensor identification information and the shape characteristic information, and extract the shape characteristic information based on the sensor identification information.

14. The shape estimation device of claim 12, wherein the sensor includes a sensor storage configured to store the shape characteristic information, and the controller is configured to extract shape characteristic information from the sensor storage.

15. An endoscope system comprising:
the shape estimation device according to claim 1; and
an endoscope including an insertion section in which the light guide is disposed;
wherein the controller is further configured to calculate a shape of the insertion section, based on the shape characteristic information.

16. The shape estimation device according to claim 1, wherein:
the light guide includes a core extending in an axial direction and a cladding layer surrounding the core, the sensing parts being provided in a part of the cladding layer;
the plurality of sensing parts are configured to absorb different amounts of light in accordance with directions of bends in the plurality of sensing parts; and
the controller is configured to calculate the shape of each of the plurality of sensing parts, including a direction of the bend in each of the plurality of sensing parts based on the light amount information detected by the photodetector.

* * * * *